(12) United States Patent
Kevil et al.

(10) Patent No.: US 11,510,925 B2
(45) Date of Patent: Nov. 29, 2022

(54) METHODS AND THERAPEUTICS TO REGULATE HYDROGEN SULFIDE BIOAVAILABILITY

(71) Applicant: Board of Supervisors of Louisiana State University and Agricultural and Mechanical College, Baton Rouge, LA (US)

(72) Inventors: Christopher G. Kevil, Shreveport, LA (US); Rodney Shackelford, Shreveport, LA (US)

(73) Assignee: Board of Supervisors of Louisiana State University, Baton Rouge, LA (US)

( * ) Notice: Subject to any disclaimer, the term of this patent is extended or adjusted under 35 U.S.C. 154(b) by 372 days.

(21) Appl. No.: 16/682,209

(22) Filed: Nov. 13, 2019

(65) Prior Publication Data
US 2020/0171041 A1     Jun. 4, 2020

Related U.S. Application Data

(60) Provisional application No. 62/760,229, filed on Nov. 13, 2018.

(51) Int. Cl.
| | | |
|---|---|---|
| *A61K 31/5377* | (2006.01) | |
| *A61K 31/519* | (2006.01) | |
| *A61K 31/275* | (2006.01) | |
| *A61K 31/105* | (2006.01) | |
| *A61K 31/497* | (2006.01) | |
| *A61K 45/06* | (2006.01) | |

(52) U.S. Cl.
CPC ........ *A61K 31/5377* (2013.01); *A61K 31/105* (2013.01); *A61K 31/275* (2013.01); *A61K 31/497* (2013.01); *A61K 31/519* (2013.01); *A61K 45/06* (2013.01)

(58) Field of Classification Search
CPC .................................................. A61K 31/5377
USPC ...................................................... 514/234.5
See application file for complete search history.

(56) References Cited

PUBLICATIONS

S.A. Yazlnski, L, Zou, Functions, Regulation, and Therapeutic Implications of the ATR Checkpoint Pathway, Atmu Rev Genet, 50 (2016) 155-173.
Kabeche, H.D. Nguyen, R. Bulsson, L. Zou, A mitosis-specific and R loop-driven ATR pathway promotes faithful chromosome segregation. Science. 359 (2018) 108-114.
R. Buisson, J.L Boisvert, C.H Benes, L, Zou, Distinct but Concerted Roles of ATR DNA-PK, and Chid in Countering Replication Stress during S Phase, Mol Cell. 59 (2015) 1011-1024.
D, Durocher, J.P. Jackson, DNA-PK, ATM and ATR as sensors of DNA damage: variations on a theme? Cutr Qpin Cell Biol, 13 (2001) 225-231.
P.C. Hanawalt, Historical perspective on the DNA damage response, DNA Repair. 36 (2015) 2-7.
S.T. Kim, Substrate specificities and identification of putative substrates of ATM kinase family members. J. Biol. Chem. 274 (1999) 37538-37543.
H. Daub, J.V, Olsen, M, Bairlein, F, Gnad, F.S. Oppermann, R. Korner, Z. Greff, G. Kert, O. Stemmann, M, Mann, Kinase-selective enrichment enables quantitative phosphoproteomics of the kinome across the cell cycle. Mol Cell. 31(2008) 438-448.
N, Dephoure, C. Zhou, J. Villen, S.A. Beausoleil, C,E, Bakalarski, SJ. Elledge, S.P Gygi, A quantitative atlas of mitotic phosphorylation, Proc Natl Acad Sci U S A. 105 (2008) 10762-10767.
S.G. Jarrett, E.M Horrell, P.A. Christian, J.C. Vanover, M,C. Boulanger, Y. Zou, J.A, D'O, PKA-Mediated Phosphorylation of ATR PRomotes Recruitment of XPA to UVInduced DNA Damage. Mol Cell. 54 (2014) 999-1011.
S.G. Jarrett, E.M Wolf Horrell, M.C. Boulanger, J,A. D'Orazio, Defining the Contribution of MC1R Phsiological Ligands to ATR Phosphorylation at Ser435, a Predictor of DNA Repair in Melanocytes. J Invest Dermatol. 135 (2015) 3086-3095.
S. Munic, J.O, Sigur&sson, Z, Xiao, T.S. Batth, G. Franciosa, L. von Stechow, Lopez-AJ. Contreras, A.C.O, Vertegaal, J.V, Olsen, Proteomics Reveals Global Regulation of Protein SUMOylation by ATM and ATR Kinases during Replication Stress. Cell Rep.21 (2017) 546-558.
E.J. Brown, D. Baltimore, ATR disruption leads to chromosomal fragmentation and early embryonic lethality. Genes Dev. 14 (2000) 397-402.
A. de Klein, M. Muijtjens, R. van Os, Y. Verhoeven, B. Smit, A.M, Carr, A.R, Lehmann, J.H. Hoeijmakers, Targeted disruption of the cell-cycle checkpoint gene ATR leads to early embryonic lethality in mice. Curr Biol. 10 (2000) 479-482.
M, O'Driscoll, V.L, Ruiz-Perez,C.G, Woods P.A. Jeggo, J.A. Goodship, A splicing mutation affecting expression of ataxia-teiangiectasia and Rad3-related protein (ATR) results in Seckel syndrome, Nat. Genet, 33 (2003) 497-501.
P. Awasthi,M. Foiani, A. Kumar, ATM and ATR signaling at a glance. J. Cell Sci, 128 (2015) 4255-4262.
K.A. Cimprich, D, Cortez, ATR: an essential regulator of genome integrity. Nat. Rev. Mol. Cell Biol. 9 (2008) 616-627.
C. Lucca, Checkpointrmediated control of repllsome-fork association and signaling in response to replication pausing. Oncogene. 23 (2004) 1206-1213.
A, Kumagai, TopBPI activates the ATR-ATRIP complex.Cell, 124 (2006) 943-955.
S, Matsuoka, ATM and ATR substrate analysis reveals extensive protein networks responsive to DNA damage, Science.316 (2007) 1160-1166.

(Continued)

Primary Examiner — Raymond J Henley, III
(74) Attorney, Agent, or Firm — Holoubek Patent Law, LLC; Charlotte Holoubek

(57) ABSTRACT

The presently claimed invention is related to compositions and methods for treating H₂S related diseases comprising administering a pharmacologically effective amount of pharmaceutical composition containing a first therapeutic, wherein the first therapeutic includes one of an ATR kinase inhibitor and an ATR kinase promotor. According to further embodiments the H₂S related disease is one of cancer, cardiovascular disease, acute inflammation, chronic inflammation, and neurological disease.

21 Claims, 18 Drawing Sheets

Specification includes a Sequence Listing.

(56) References Cited

PUBLICATIONS

E.M, Hammond, M.J, Doric, A.J. Giacci'a, ATR/ATM targets are phosphorylated by ATR in response to hypoxia and ATM in response to reoxygenation. J, Biol. Chem. 278 (2003) 12207-12213.

W, Jeremy, P, Yogin, B.L. Lentz, Y.S, Yan, APE2 is required for ATR-Chkl checkpoint activation in response to oxidative stress, Proc. Natl. Acad. Sci, U S A. 110 (2013) 10592-10597.

A. Kulkarni, K.C. Das, Differential roles of ATR and ATM in p53, Chkl, and histone H2AX phosphorylation in response to liyperoxia: ATR-dependent ATM activation. Am. J, Physiol. Lung Cell. Mol, Physiol, 294 (2008) L998-L1006.

PJ. Hurley, D, Wilsker, F, Bunz, Human cancer cells require ATR for cell cycle progression following exposure to ionizing radiation. Oncogene 26 (2007) 2535-2542.

G.K. Kolluru, X, Shen, S, Yuan, C.G. Kevil, Gasotransmitter heterocellular signaling. Antioxid.Redox Signal, 26 (2017) 936-960.

H. Kimura, Production and physiological effects of hydrogen sulfide, Antioxid. Redox Signal. 20 (2014) 783-793.

M.S. Attene-Ramos, E.D. Wagner, H.R, Gaskins, M.J, Plewa, Hydrogen sulfide induces, direct radical-associated DNA damage, Mol Cancer Res. 5 (2007) 455-459.

M.S. Attene-Ramos, G.M. Nava, M.G. Muelhier, E.D. Wagner, M.J, Plewa, H.R Gaskins, DNA damage and toxicogenomic analyses of hydrogen sulfide in human intestinal epithelialFHs 74 intcells, EnvironMoi Mutagen, 51 (2010) 304-314.

B, Deplancke, H.R. Gaskins, Hydrogen sulfide induoes serum-independent cell cycle entry in nontransformed rat intestinal epithelial cells. FASEB J. 17 (2.003) 1310-1312.

Y, Pei, B, Wu, Q. Cao, L. Wu, G. Yang, Hydrogen sulfide mediates the anti-survival effect of sulbraphane on human prostate cancer cells. Toxicol Appl Phaimacol.257 (2011) 420428.

M.R. Hellmich, C. Szabo, Hydrogen Sulfide and Cancer. Handb Exp Pharmacol. 230 (2015) 233-241.

P.J. Hurley, D. Wilsker, F. Bunz, Human cancer cells require ATR for cell cyole progression following exposure to ionizing radiation. Oncogene. 2007 26 (2007) 2535-2542.

R,E, Shackelford, Y. Fu, R.P. Manuszak, T.C. Brooks, A.P Sequeira, S, Wang, M. Lowery-Nordberg, A. Chen, Iron chelators reduce chromosomal breaks in ataxiatelangiectasia cells.DNA Repair. 5(2006) 1327-1336.

A. Leskova, S, Pai'dije, J.D. Glawe, C.G Kevil, X. Shen, Role of thiosulfate In hydrogen sulfide-dependent redox signaling in endothelial cells, Am J Physiol Heart Ciro Physiol. 313 (2017) H256-H264.

X. Shen, E,A, Peter, S. Bir, R. Wang, C.G. Kevil. Analytical measurement of discrete hydrogen sulfide pools in biological specimens, Free Radio Biol Med. 15 (2012;2276-2283.

R, Sanokawa-Akakura, E.A. Ostrakhovitch, S. Akakura, S. Goodwin, S, Tablbzadeh. A H2S-Nampt dependent energetic circuit is critical to survival and cytoprotection from damage in cancer cells. PLoS One. 9 (2014)e108537.

R. Shackelford, J, Abdulsattar, E, Wei, J. Cotelingam, D. Coppola, G. Herrera, Increased Nicotinamide Phosphoribosyltransferase and Cystathionine [3-Synthase in Renal Oncocytomas, Renal Transitional Cell Carcinoma and Renal Clear Cell Carcinoma, Anticancer Research 37 (2017) 3423-3427.

S, Patel, J, Ansari, A, Meram, J.Abdulsattar, J, Cotelingam, D, Coppola D, G. Ghali G, R, Shackelford, Increased nicotinamide phosphoribosyltransferase and CystathionineBeta-Synthase in oral cavity squamous cell carcinomas , International Journal of Clinical and Experimental Medicine, 10 (2017) 702-707.

H. Capasso, C. Palermo, S, Wan, H. Rao, U.P. John, M.J. O'Connell, N.C, Walworth, Phosphorylation activates Chkl and is required for checkpoint-mediated cell cyole arrest J Cell Set, 115 (2002) 4555-4564.

S. Burma, B.P, Chen, M, Murphy, A, Kurimasa, D.J. Chen. ATM phosphorylates histone H2AX in response to DNA double-strand breaks. J Biol Chem, 276 (2001) 42462-42467.

Z, Qiu, N.L Oleinick, J. Zhang, ATR/CHK1 inhibitors and cancer therapy.Radiother Oncol. 126(2018) 450-464.

D. Wu, W. Si, M, Wang, S. Lv, A. Ji, Y, Li, Hydrogen sulfide in cancer: Friend or foe? Nitric Oxide. 50 (2015) 38-45.

\* P < 0.05

| Gene | Species | Forward | Reverse |
|---|---|---|---|
| GAPDH | Human | ACAGTCAGCCGCATCTTC | CGCCCAATACGACCAAATC |
| CSE | Human | GCCTTTGCTTCAGGTTTAGC | CCTTCTGGGTGGGGTTTGT |
| CBS | Human | AGGATGAACACAGGCAAT | AAAAACCCAAACACGCAAAC |
| 3-MST | Human | ACCGTGAACATCCCCTTC | TTCTTCTCCTGGAACAGATG |

FIG. 9

METHODS AND THERAPEUTICS TO REGULATE HYDROGEN SULFIDE BIOAVAILABILITY

CROSS REFERENCE TO RELATED APPLICATIONS/PRIORITY

The present invention claims priority to U.S. Provisional Patent Application No. 62/760,229 filed Nov. 13, 2018, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

BACKGROUND

Various human and animal diseases influenced by the amount of hydrogen sulfide bioavailability exist, which afflict millions of individuals, but for which there can be limited or no therapeutics. For such reasons, there is a pressing, but seemingly irresolvable need for more effective methods and therapeutics for regulate hydrogen sulfide bioavailability.

SUMMARY

Wherefore, it is an object of the present invention to overcome the above mentioned shortcomings and drawbacks associated with the current technology.

The presently claimed invention is related to compositions and methods for treating $H_2S$ related diseases comprising administering a pharmacologically effective amount of pharmaceutical composition containing a first therapeutic, wherein the first therapeutic includes one of an ATR kinase inhibitor and an ATR kinase promotor. According to further embodiments the $H_2S$ related disease is one of cancer, cardiovascular disease, acute inflammation, chronic inflammation, and neurological disease. According to further embodiments the H2S disease is human colorectal cancer. According to further embodiments the first therapeutic includes an ATR kinase inhibitor. According to further embodiments the ATR kinase inhibitor is one of NU6027, AZD6738, BAY1895344, VX-803, and VX-970. According to further embodiments the first therapeutic includes an ATR kinase promotor. According to further embodiments the ATR kinase promotor is one of ETAA1 (Ewing's tumor-associated antigen 1) and TopBP1. According to further embodiments the pharmaceutical composition further contains a second therapeutic distinct from the first therapeutic. According to further embodiments the second therapeutic includes one of H2S, an H2S suppressor, an H2S promotor and a cystathionine beta-synthase (CBS) inhibitor and/or a cystathionine gamma-lyase (CSE) inhibitor The presently claimed invention is further related to compositions and methods of affecting H2S bioavailability in a mammal comprising administering a pharmacologically effective amount of pharmaceutical composition containing a first therapeutic, wherein the first therapeutic includes one of an ATR kinase inhibitor and an ATR kinase promotor. According to further embodiments method includes a step of increasing H2S bioavailability. According to further embodiments method includes the step of decreasing H2S bioavailability. According to further embodiments the first therapeutic includes an ATR kinase inhibitor. According to further embodiments the first therapeutic includes an ATR kinase promotor. According to further embodiments the pharmaceutical composition further contains a second therapeutic distinct from the first therapeutic.

The presently claimed invention is still further related to methods and pharmaceutical compositions comprising a first therapeutic and a second therapeutic, wherein the first therapeutic is one of an ATR kinase promotor and an ATR kinase inhibitor, and the first therapeutic is chemically distinct from the second therapeutic. According to further embodiments the first therapeutic is the ATR kinase promotor. According to further embodiments the first therapeutic is the ATR inhibitor. According to further embodiments the second therapeutic is a H2S promotor. According to further embodiments the second therapeutic is a H2S inhibitor.

The present invention relates to pharmaceutical compositions of a therapeutic (e.g., an ATR kinase promotor or an ATR kinase inhibitor), or a pharmaceutically acceptable salt, solvate, ester, amide, clathrate, stereoisomer, enantiomer, prodrug or analogs thereof, and use of these compositions for the treatment of a $H_2S$ related disease, including cancer, cardiovascular disease, acute inflammation, chronic inflammation, and neurological disease.

In some embodiments, the therapeutic is administered as a pharmaceutical composition that further includes a pharmaceutically acceptable excipient.

In some embodiments, administration of the pharmaceutical composition to a human results in a peak plasma concentration of the therapeutic between 0.05 µM-10 µM (e.g., between 0.05 µM-5 µM).

In some embodiments, the peak plasma concentration of the therapeutic is maintained for up to 14 hours. In other embodiments, the peak plasma concentration of the therapeutic is maintained for up to 1 hour.

In some embodiments, the condition is a $H_2S$ related diseases.

In certain embodiments, the $H_2S$ related disease is mild to moderate $H_2S$ related disease.

In further embodiments, the $H_2S$ related disease is moderate to severe $H_2S$ related disease.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

In some embodiments, the pharmaceutical composition is administered concurrently with one or more additional therapeutic agents for the treatment or prevention of the $H_2S$ related diseases.

In some embodiments, the therapeutic, or a pharmaceutically acceptable salt, solvate, or prodrug thereof, is administered as a pharmaceutical composition that further includes a pharmaceutically acceptable excipient.

In some embodiments, administration of the pharmaceutical composition to a human results in a peak plasma concentration of the therapeutic between 0.05 µM-10 µM (e.g., between 0.05 µM-5 µM).

In some embodiments, the peak plasma concentration of the therapeutic is maintained for up to 14 hours. In other embodiments, the peak plasma concentration of the therapeutic is maintained for up to 1 hour.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

As used herein, the term "delayed release" includes a pharmaceutical preparation, e.g., an orally administered formulation, which passes through the stomach substantially intact and dissolves in the small and/or large intestine (e.g., the colon). In some embodiments, delayed release of the active agent (e.g., a therapeutic as described herein) results from the use of an enteric coating of an oral medication (e.g., an oral dosage form).

The term an "effective amount" of an agent, as used herein, is that amount sufficient to effect beneficial or desired results, such as clinical results, and, as such, an "effective amount" depends upon the context in which it is being applied.

The terms "extended release" or "sustained release" interchangeably include a drug formulation that provides for gradual release of a drug over an extended period of time, e.g., 6-12 hours or more, compared to an immediate release formulation of the same drug. Preferably, although not necessarily, results in substantially constant blood levels of a drug over an extended time period that are within therapeutic levels and fall within a peak plasma concentration range that is between, for example, 0.05-10 µM, 0.1-10 µM, 0.1-5.0 µM, or 0.1-1 µM.

As used herein, the terms "formulated for enteric release" and "enteric formulation" include pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

The term "immediate release" includes where the agent (e.g., therapeutic), as formulated in a unit dosage form, has a dissolution release profile under in vitro conditions in which at least 55%, 65%, 75%, 85%, or 95% of the agent is released within the first two hours of administration to, e.g., a human. Desirably, the agent formulated in a unit dosage has a dissolution release profile under in vitro conditions in which at least 50%, 65%, 75%, 85%, 90%, or 95% of the agent is released within the first 30 minutes, 45 minutes, or 60 minutes of administration.

The term "pharmaceutical composition," as used herein, includes a composition containing a compound described herein (e.g., an ATR kinase promotor or ATR kinase inhibitor, or any pharmaceutically acceptable salt, solvate, or prodrug thereof), formulated with a pharmaceutically acceptable excipient, and typically manufactured or sold with the approval of a governmental regulatory agency as part of a therapeutic regimen for the treatment of disease in a mammal.

Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, includes any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, includes those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, includes those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, oleate, oxalate, palm itate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylam ine, dimethylamine, trimethylamine, triethylamine, ethylamine, and the like.

The terms "pharmaceutically acceptable solvate" or "solvate," as used herein, includes a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, includes prophylactic treatment or treatment that prevents one or more symptoms or conditions of a disease, disorder, or conditions described herein (e.g., $H_2S$ related diseases). Treatment can be initiated, for example, prior to ("pre-exposure prophylaxis") or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, includes compounds which are rapidly transformed in vivo to the parent compound of the above formula. Prodrugs also encompass bioequivalent compounds that, when administered to a human, lead to the in vivo formation of therapeutic. Preferably, prodrugs of the compounds of the present invention are pharmaceutically acceptable.

As used herein, and as well understood in the art, "treatment" includes an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also include delaying the onset of, impeding or reversing the progress of, or alleviating either the disease or condition to which the term applies, or one or more symptoms of such disease or condition.

The term "unit dosage forms" includes physically discrete units suitable as unitary dosages for human subjects and other mammals, each unit containing a predetermined quantity of active material calculated to produce the desired therapeutic effect, in association with any suitable pharmaceutical excipient or excipients.

As used herein, the term "plasma concentration" includes the amount of therapeutic present in the plasma of a treated subject (e.g., as measured in a rabbit using an assay described below or in a human).

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

INCORPORATION OF SEQUENCE LISTING (TEXT FILE)

This application contains a text file named p51aus ST25.txt, which is 1,520 bytes (measured in MS-DOS), which was created on Feb. 19, 2020, and is hereby incorporated by reference in to the specification of this application in its entirety. The text file sequence listing contains the PCR primer sequence listings that are listed in FIG. 9 of the Drawings.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIG. 2A shows $H_2S$ concentrations were compared in ATR and ATR-H, with and without the ATR kinase inhibitor NU6027. The cells were treated for two hours with 12 μM NU6027 in standard media and harvested (2 A). FIG. 2B shows $H_2S$ concentrations were compared in ATR and ATR-H, with and without the CBS and CSE inhibitor β-cyanol-l-alanine. The cells were treated with 1 mM β-cyano)-l-alanine for two hours in standard media and harvested (2B). FIG. 2C shows $H_2S$ concentrations were compared in ATR and ATR-H, with and without 20 μM diallyl trisulfide for two hours in standard media and harvested (2C). "βCA"=1 mM β-cyano)-l-alanine. Free $H_2S$ is in nmol/mg protein.

In FIG. 5B, ATR and ATR-H cells were treated with 100 μM t-BOOH for 15 min, incubated in standard media for 45 min, and harvested. In FIG. 5C, ATR and ATR-H cells were treated with 15,000 μJ/cm$^2$UV light and the cells were harvested 45 min later.

FIG. 9 is a table that lists the primers used in the quantitative real-time polymerase chain reactions of FIGS. 4A-4C. GADPH was used as a control.

DETAILED DESCRIPTION

Figure 1:
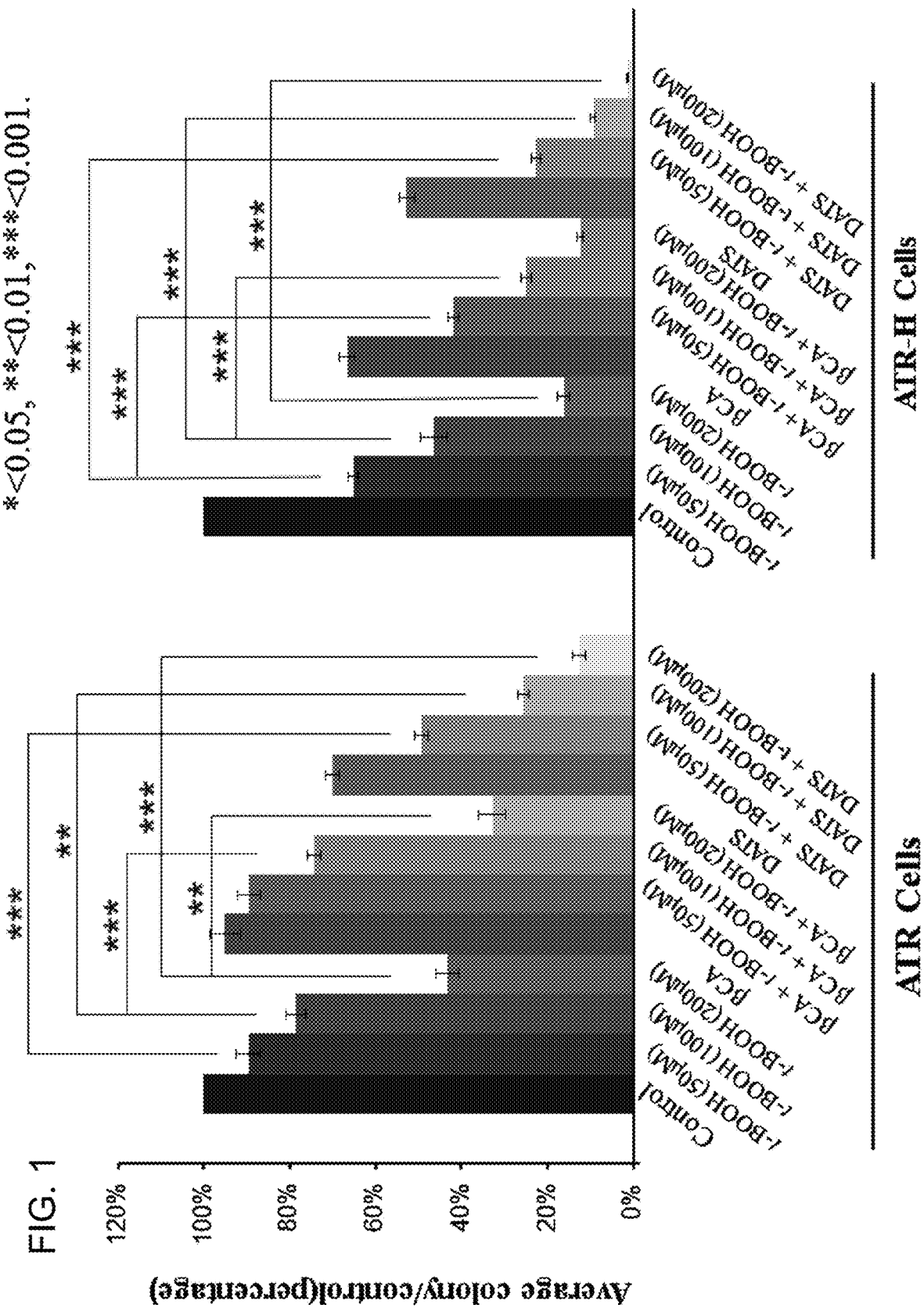
FIG. 1 shows the effects of t-BOOH and $H_2S$ inhibitor and donor treatments in the colony-forming efficiency assay with ATR and ATR-H cells. Twelve hours after plating in appropriate media, exponentially growing ATR and ATR-H cells were treated for two hours with either an $H_2S$ inhibitor (1 mM β-cyano-1-alanine, βCA) or an $H_2S$ donor (20 μM diallyl trisulfide, DATS), and subjected to 15 min 50, 100, or 200 μM t-BOOH oxidative stress. After 11 days, the cells were fixed, stained, and the colonies counted. Data indicates survival as a percentage of untreated cells.

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40% means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIG. 1, a brief description concerning the various components of the present invention will now be briefly discussed.

The ataxia telangiectasia-mutated and Rad3-related (ATR) serine/threonine kinase plays a central role in the repair of replication-associated DNA damage, the maintenance of S and G2/M-phase genomic stability, and the promotion of faithful mitotic chromosomal segregation. A number of stimuli activate ATR, including persistent single-stranded DNA at stalled replication forks, R loop formation, hypoxia, ultraviolet light, and oxidative stress, leading to ATR-mediated protein phosphorylation. Recently, hydrogen sulfide ($H_2S$), an endogenous gasotransmitter, has been found to regulate multiple cellular processes through complex redox reactions under similar cell stress environments. Three enzymes synthesize $H_2S$: cystathionine-β-synthase, cystathionine γ-lyase, and 3-m ercaptopyruvate sulfurtransferase. Since $H_2S$ can under some conditions cause DNA damage, the inventors hypothesized that ATR activity may regulate cellular $H_2S$ concentrations and $H_2S$-syntheszing enzymes. The inventors disclose herein that human colorectal cancer cells carrying biallelic knock-in hypomorphic ATR mutations have lower cellular $H_2S$ concentrations than do syngeneic ATR wild-type cells, and all three $H_2S$-synthesizing enzymes show lower protein expression in the ATR hypomorphic mutant cells. Additionally, ATR serine 428 phosphorylation is altered by $H_2S$ donor and $H_2S$ synthesis enzyme inhibition, while the oxidative-stress induced phosphorylation of the ATR-regulated protein CHK1 on serine 345 is increased by $H_2S$ synthesis enzyme inhibition. Lastly, inhibition of $H_2S$ production potentiated oxidative stress-induced double-stranded DNA breaks in the ATR hypomorphic mutant compared to ATR wild-type cells. These disclosed findings demonstrate that the ATR kinase regulates and is regulated by $H_2S$.

The ataxia telangiectasia-mutated and Rad3-related (ATR) serine/threonine kinase plays a central role in maintaining genomic stability. Located at 3q23, ATR consists of a 2,644-amino acid residue phosphatidylinositol 3-kinase-related family member with overlapping sequence and functional homologies to the DNA-dependent and ataxia telangiectasia-mutated protein kinases. Together, these proteins are central in coordinating the DNA damage response (DDR) which functions to recognize DNA damage and initiate intracellular pathways that repair genomic damage. The ATR consensus phosphorylation site occurs at serine or threonine residues followed by glutamine residues (SQ/TQ), with kinase activation correlating with ATR serine 435 (ATR-pS435) and threonine 1989 (ATR-pT1989) phosphorylations. Specifically ATR-pS435 is required for ATR-XPA complex formation, which promotes nucleotide excision repair at sites of photodamaged DNA. ATR also regulates the small ubiquitin like modifier (SUMO) system, particularly the sumoylation of proteins that protect cells from replication stress and fork breakage.

ATR was first identified as being essential for embryonic development with ATR-deficient mouse embryos showing inviability, accompanied by shattered chromosomes. Individuals with hypomorphic ATR mutations have Seckel syndrome type 1, characterized by primordial dwarfism, avian faces, accelerated aging, micrognathia, microcephaly, growth retardation, intellectual disability, and defects in the DDR. Complete ablation of ATR function results in rapid cell death.

ATR maintains genomic stability by safeguarding replication S-phase fork integrity, regulating cell cycle progression, initiating cell cycle checkpoints following genotoxic insults, and by associating with centromeres where it promotes faithful chromosomal segregation at mitosis. Specifically, ATR recognizes single-stranded DNA (ssDNA) coated by Replication Protein A, which commonly occurs following DNA damage or at stalled DNA replication folks. In combination with other proteins (including ATRIP, TopBP1, and the 911 complex), ATR phosphorylates multiple protein substrates, including the checkpoint kinase 1 (CHK1), initiating cellular DNA damage responses. ATR is also activated by hypoxia, cellular mechanical, and oxidative stressors].

Hydrogen sulfide ($H_2S$) is an important cellular gasotransmitter, functioning in neuromodulation, cytoprotection, oxygen sensing, angiogenesis, and vascular tone regulation. $H_2S$ is synthesized by three enzymes: cystathionine-β-synthase (CBS), cystathionine γ-lyase (CSE), and 3-mercaptopyruvate sulfurtransferase (3-MST). Presently there is no data in the art demonstrating a role for $H_2S$ in the DDR or ATR activities. However, under certain conditions $H_2S$ can directly induce DNA damage, suggesting that it could activate the DDR. Additionally, $H_2S$ can either promote or suppress cell cycle progression, likely due to lower endogenous $H_2S$ concentrations promoting cell proliferation and higher $H_2S$ concentrations inhibiting it. Since ATR responds to DNA damage, the inventors hypothesized that it may play a role in regulating cellular $H_2S$ concentrations and levels of the $H_2S$-synthesizing enzymes. The inventors examined the role of the ATR kinase in $H_2S$ regulation.

2.1. Materials: Monobromobimane (MBB), Tris (2-carboxyethyl)phosphine hydrochloride (TCEP), sulfosalicylic acid (SSA), 1-fluoro-2,4-dinitrobenzene (DNFB), TPP® tissue culture dishes, NU6027, penicillin/streptomycin, and t-BOOH were purchased from Sigma (St. Louis, Mo.). Fetal bovine serum, Dulbecco's modified Eagle's medium (DMEM) (standard liquid media) were from Invitrogen (Rockville, Md.). β-cyano-1-alanine and diallyl trisulfide were purchased from the Cayman Chemical Company (Ann Arbor, Mich.). Antibodies used were anti-ATR-p5435 (Cell Signaling Technology Inc, Danvers, Mass., catalog number 2853s), anti-total-ATR (Invitrogen, Waltham, Mass. USA, catalog number PA1-450), anti-CHK1-pS345 (Invitrogen, catalog number PA5-34625), anti-total-CHK1(Abcam, Cambridge, Mass., catalog number ab47574), anti-3-MST (Santa Cruz Biotechnology, Santa Cruz, Calif., catalog number sc-135993), anti-CSE (Santa Cruz Biotechnology, catalog number sc-101924), anti-CBS (Santa Cruz Biotechnology, catalog number sc-67154), and anti-Visfatin (Nampt, Bethyl Laboratories, Montgomery Tex., catalog number A300-779 A), rabbit anti-GADPH (Sigma, catalog number G9545), and anti-beta-actin (abcam, catalog number ab8227). Secondary antibodies were goat anti-rabbit IgG (catalog numbers ab6721 & ab2040, Abcam), goat anti-mouse IgG (catalog number ab205719, Abcam), and goat anti-mouse IgG (catalog number sc358920, Santa Cruz).

Cells: The human colon cancer cell line DLD1 cell line containing wild-type ATR (ATR cells) or the ATR-Seckel knock-in hypomorphic mutation (ATR-H cells) were a kind gift from Dr. Fred Bunz of the Department of Radiation Oncology and Molecular Radiation Sciences, The Johns Hopkins University School of Medicine. The cells were cultured in DMEM with 5% FBS, 1% penicillin/streptomycin. Only low-passage cells were used to avoid the possibility that high passage ATR-H cells might lose the hypomorphic mutation and hence be altered.

Colony forming-efficiency assay: Colony forming-efficiency (CEFA) experiments were performed. In brief, exponentially growing cells were plated for 12 h at 2000 cells/100 mm tissue culture dish in 10 ml appropriate media. The cells were pretreated for 2 h with either an $H_2S$ inhibitor (β-cyano-1-alanine, 1 mM) or donor (diallyl trisulfide, 20 uM), washed 3× with 1× phospate buffered saline, the media replaced, and the cells were immediately treated with for 15 min with 50, 100, and 200 μM t-butyl hydroperoxide (t-BOOH). Following treatment, the cells were washed 3× with phosphate-buffered saline, the media replaced and the cells cultured for 11 days. The resulting colonies were fixed and stained by water: methanol addition (1:1) containing crystal violet (1 g/l). "Colonies" consisted of cell clusters containing greater than 50 cells when counted by dissecting microscopy.

$H_2S$ measurements: Bioavailable sulfide levels were measured as previously reported. Levels of free sulfide ($H_2S$) in ATR and ATR-H cells were measured by high performance liquid chromatography (HPLC) after derivatization with excess MBB as stable products sulfide-dibimane (SDB).

Briefly, ATR and ATR-H cells were homogenized in Tris.HCl buffer [100 mM Tris.HCl (pH 9.5) and 0.1 mM diethylenetriaminepentaacetic acid (DTPA)]. Cell lysates were derivatized with MBB and then measured by Shimadzu Prominence 20 A equipment with RF-10AXL (excitation wavelength: 390 mm and emission wavelength: 475 mm) and an Eclipse XDB-C18 column (4.6×50 mm, 5 µm). Typical retention times of SDB were 16.5 min. $H_2S$ levels were calculated according to the standard SDB.

Western blotting: To prepare whole cell lysates from ATR and ATR-H cells, the cells were grown in 6-well plates, the medium was removed, and 300 µl of SDS sample buffer (62.5 mM Tris-HCl (pH 6.8), 2% w/v SDS, 10% glycerol, 50 mM dithiothreitol, 0.1% w/v bromphenol blue) was added to each well. Following lysis in SDS sample buffer, lysates were harvested with cell scrapers and collected in Eppendorf tubes. The lysates were boiled, centrifuged, and frozen at −20° C. until gel electrophoresis was performed. The protein concentrations were measured by Bio-rad DC protein assay. Twenty pgs of total protein supernatant extract was mixed with 2×SDS loading buffer according to protein concentration. Lysates separated by SDS-PAGE were transferred to polyvinylidene difluoride membranes, and membranes were blocked in 5% nonfat dry milk before the addition of primary antibodies. Densitometry was performed with ImageJ software version 1.45 s. All western blots were performed at least in triplicate.

Quantitative real-time polymerase chain reaction: Total cellular RNA was isolated from ATR and ATR-H cultured cells using Trizol according to the manufacturer's instruction. One µg of RNA was reverse transcribed using iScript cDNA synthesis kit (Bio-rad, 1708891). Quantitative real-time polymerase chain reaction was performed using SYBR Green Master Mix (Bio-rad, 1708882), and gene expression was quantified using the $2^{-\Delta\Delta C_T}$ method. All genes of interest were normalized to the housekeeping gene GAPDH. The primers used in polymerase chain reaction reactions are listed in the table in FIG. 9. FIG. 9 shows the forward and reverse primers used to quantify CBS, CSE, and 3-MST mRNA levels in ATR and ATR-H cell lines in FIGS. 4A-4C. GAPDH primers were used for control normalizations.

Ultraviolet ATR and ATR-H cell treatment: ATR and ATR-H cells were treated with ultraviolet (UV) light by removing the media from the tissue culture dishes and exposing the cells to UV light using a CL-1000 UV Crosslinker (UVP/Analytik Jena, Atkinson, N.H., USA) at 15,000 µJ/cm² (150×100 µJ/cm²). Following UV treatment, media was replaced and the cells were incubated for 45 min and harvested. Untreated cells were subjected to the same procedures without the UV exposure.

Chromosomal preparation and analysis: One 100-mm tissue culture plate/treatment of logarithmically growing ATR and ATR-H cells at 50% confluence were treated with or without, 1 mM $H_2S$ inhibitor β-cyano-l-alanine for two hours, followed by a 15-minute treatment with 10 µM t-BOOH. Following this treatment, the cells were washed 3× with phosphate-buffered saline, the media replaced, and the cells cultured for 1 h. Colcemid (100 ng/ml) was then added for 4 h and the cells harvested by washing 2× in 1×PBS, followed by trypsinization and transference to a 15 ml tube. Two-ml of DMEM with 5% FBS was added/tube and the cells were pelleted 5 min at 500×g. The cells were resuspended in 5 ml 0.075 mM KCl and incubated 15 min at 37° C. About 200 µl of fresh methanol: glacial acetic acid at 3:1 (Carnoy's fixative) was added, the cells gently vortexed, and pelleted for 5 min at 500×g. The supernatant was removed and 5 ml of Carnoy's fixative added with gentle vortexing. The cells were pelleted for 5 min at 500×g, the supernatant removed, and 5 ml of Carnoy's fixative was added with gentle vortexing. Chromosomal preparations were made by pelleting the preparations for 5 min at 500×g, removing the supernatant, dropping on slides, drying for 30 min at 90° C., Giemsa staining, washing, and cover-slipping. Each data point represents 5000 individual chromosomal observations preformed under oil immersion microscopy done in triplicate.

Statistical analysis: The significance for all the experiments in this paper were calculated by using prism software version 5.02 (GraphPad Inc., San Diego, Calif.). The P values are given in each figure.

Results

Compared to ATR wild-type cells, syngeneic ATR-H cells are preferentially sensitive to oxidative stress following H2S modulators in the CEFA. To initiate these studies, colony efficiency formation in ATR and ATR-H cells was examined with either pharmacologic $H_2S$ inhibition or $H_2S$ supplementation, followed by a 15-minute treatment with 50, 100, or 200 µM t-BOOH, culturing for 11 days, followed by fixation and analysis. As shown in FIG. 1, the ATR-H cells exhibited greater sensitivity to increasing t-BOOH exposures compared to ATR cells. Pretreatment with the $H_2S$ inhibitor (2 h with 1 mM β-cyano-l-alanine) followed by the same t-BOOH exposures, slightly increased the sensitivity of the ATR cells to different t-BOOH concentrations. Under the same conditions, the ATR-H cells were significantly more sensitive to the same t-BOOH exposures compared to the syngeneic ATR wild-type cells, (FIG. 1). For both cell types, colony formation suppression was t-BOOH dose-dependent and interestingly, β-cyano-1-alanine by itself suppressed ATR-H cell colony formation. $H_2S$ donor pretreatment (2 h with 20 µM diallyl trisulfide) significantly decreased ATR and ATR-H cell colony formation, with the ATR-H cells significantly more sensitive to the $H_2S$ donor (FIG. 1). Based on the above data, we conclude that the ATR hypomorphic mutation confers increased cellular sensitivity to pharmacologic perturbations in $H_2S$ metabolism, both with and without exogenous oxidative stress.

Figure 2A:
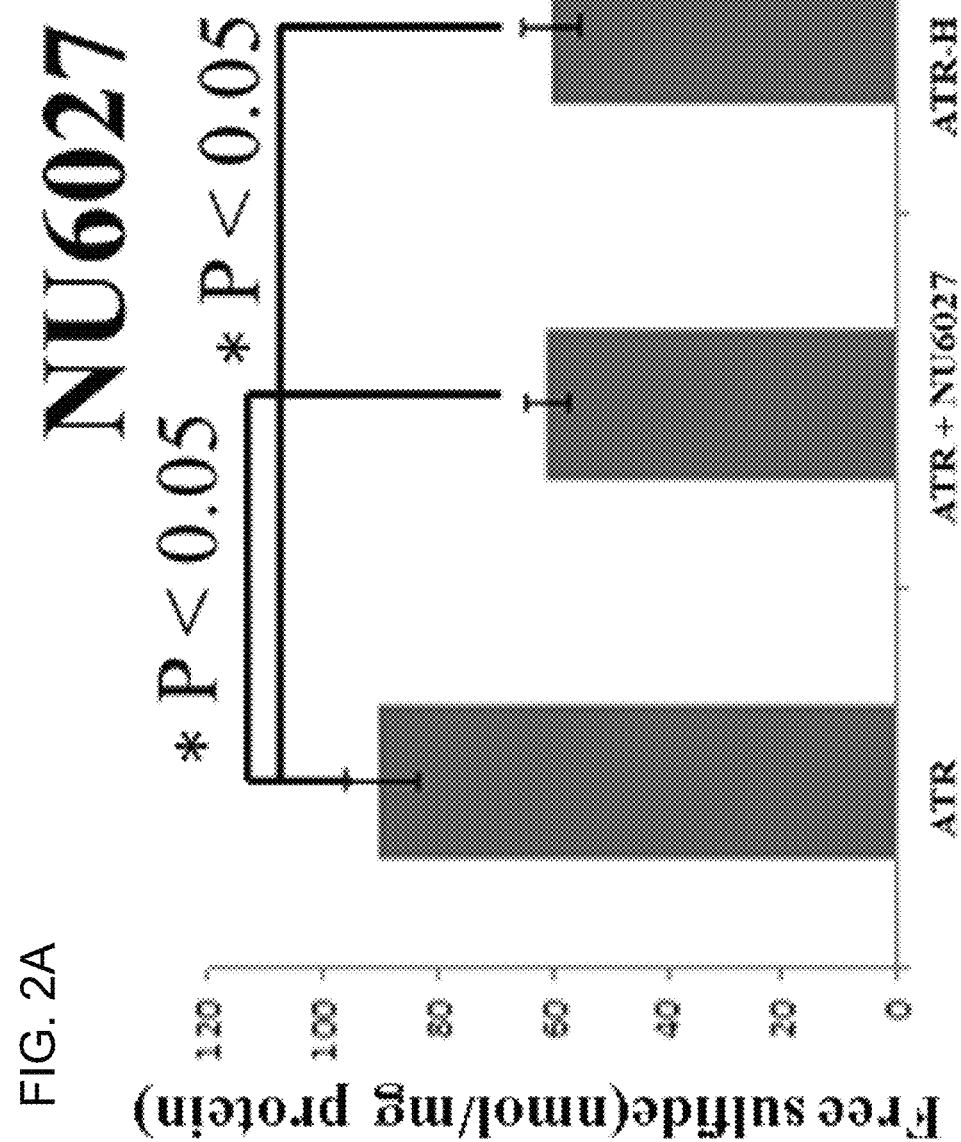
FIGS. 2A-2C show free cellular $H_2S$ concentrations in the ATR wild-type cells compared to the ATR-H mutant cells.
Figure 2B:
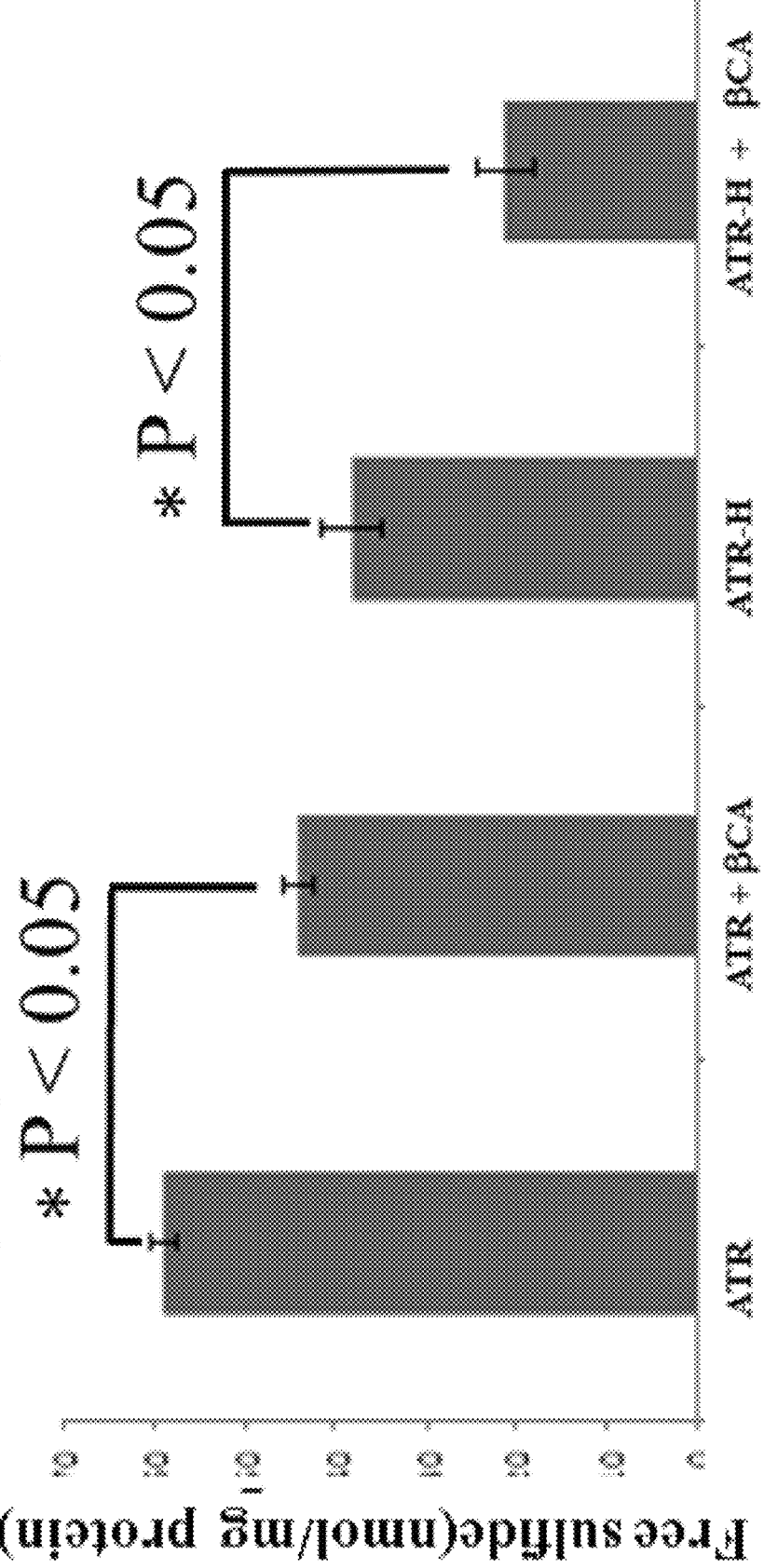
Figure 2C:
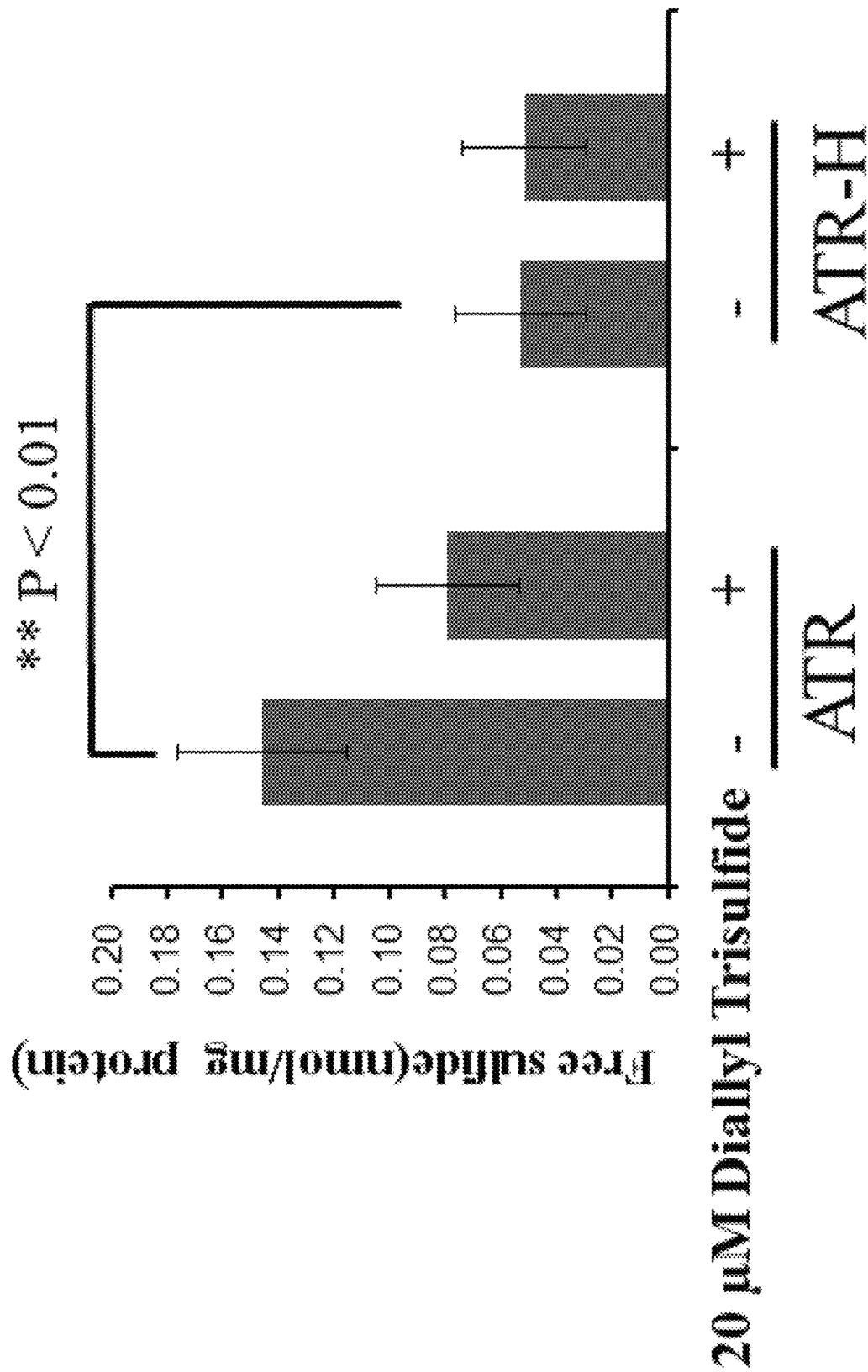

Cellular $H_2S$ concentrations are lower in the hypomorphic ATR-H mutants compared to wild-type ATR cells. The inventors used HPLC to analyze cellular $H_2S$ levels following MBB derivatization. As shown in FIG. 2A, free $H_2S$ was significantly lower in the ATR-H cells compared to the ATR cells. Additionally, a 2 h treatment with 12 µM NU6027, an ATR inhibitor, significantly decreased the cellular free $H_2S$ concentrations in the ATR, but not the ATR-H cells (FIG. 2A). In addition, as shown in FIG. 2B, a 2 h treatment with 1 mM $H_2S$ synthesis inhibitor β-cyano-1-alanine significantly lowered free $H_2S$ concentrations in both cell types, demonstrating that this $H_2S$ inhibitor worked in the inventors' assays. Last, ATR and ATR-H cells were treated 2 h with 20 µM diallyl trisulfide. As shown in FIG. 2C, diallyl trisulfide treatment suppressed the cellular free $H_2S$ concentrations in the ATR, but not the ATR-H cells. Thus, cellular $H_2S$ levels are diminished by two different perturbations of ATR activity, the hypomorphic Seckel syndrome ATR mutation and ATR protein inhibition by NU6027 (FIG. 2A). Additionally, exogenous $H_2S$ suppressed cellular $H_2S$ levels in the wild-type cells, but not the hypomorphic mutants, indicating possible differences in cellular $H_2S$ processing due to the hypomorphic mutant ATR protein.

Figure 3A:
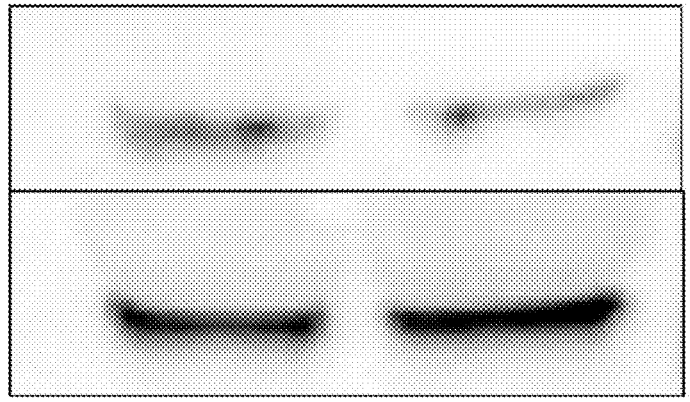
FIG. 3A-3D show representative western blots for CBS (FIG. 3 A), CSE (FIG. 3B), 3-MST (FIG. 3C), and Nampt (FIG. 3D) comparing ATR and ATR-H cells protein expression with β-actin as a control protein. All western blots were performed at least in triplicate.
Figure 3A:
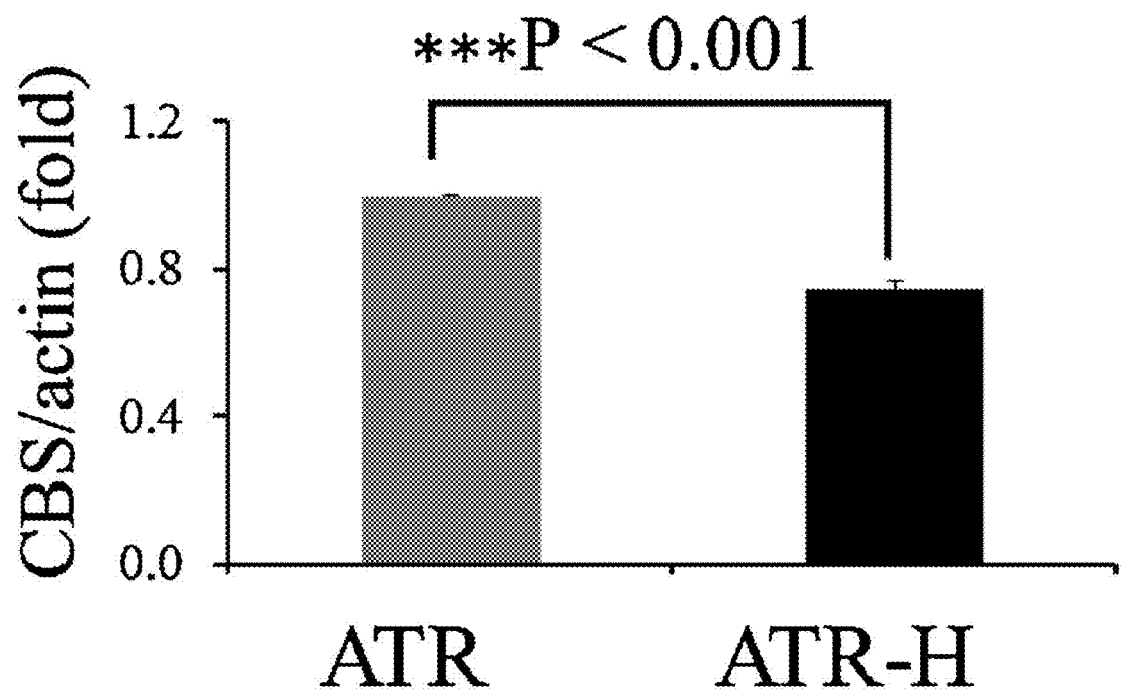
Figure 3B:
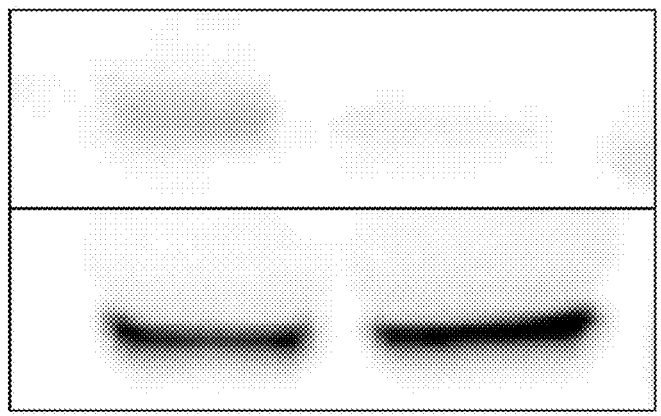
Figure 3B:
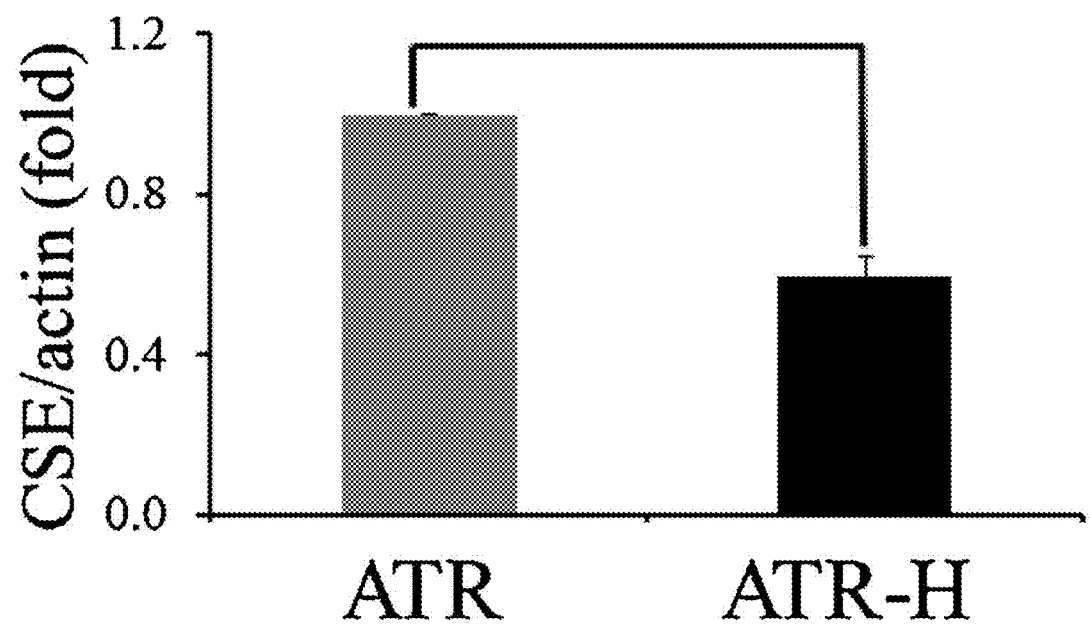
Figure 3C:
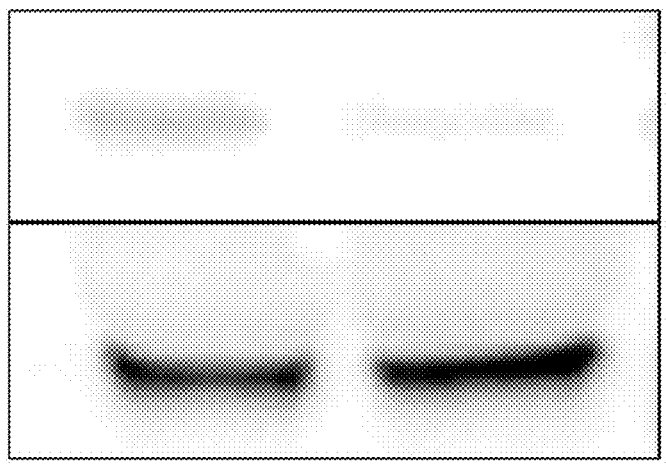
Figure 3C:
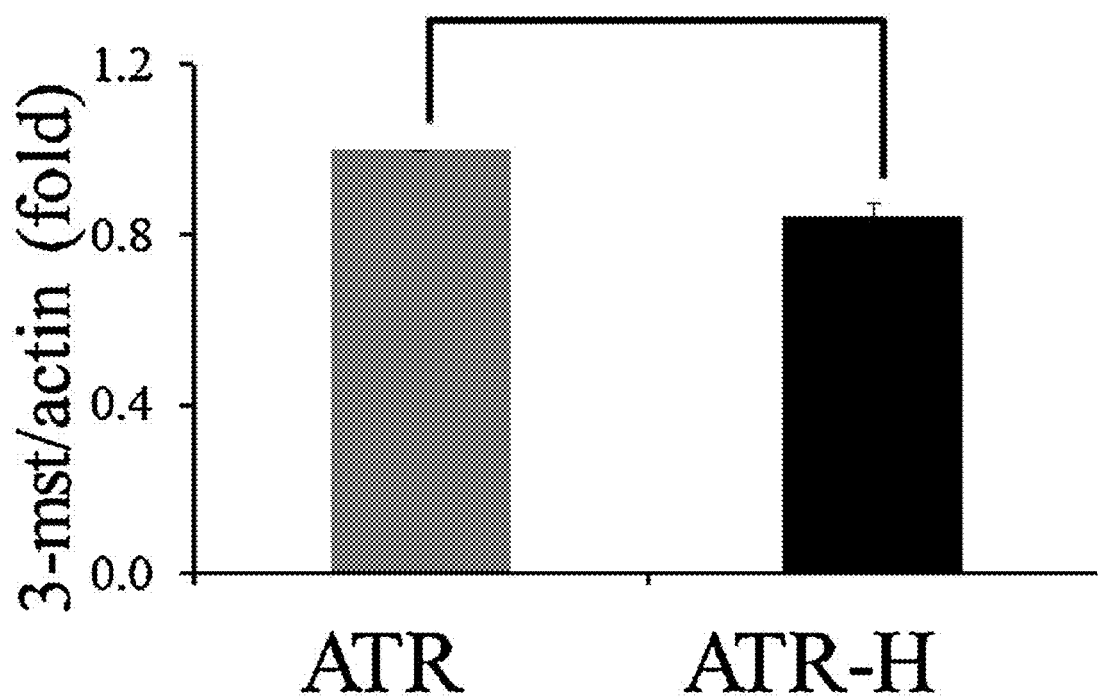
Figure 3D:
Figure 3D:
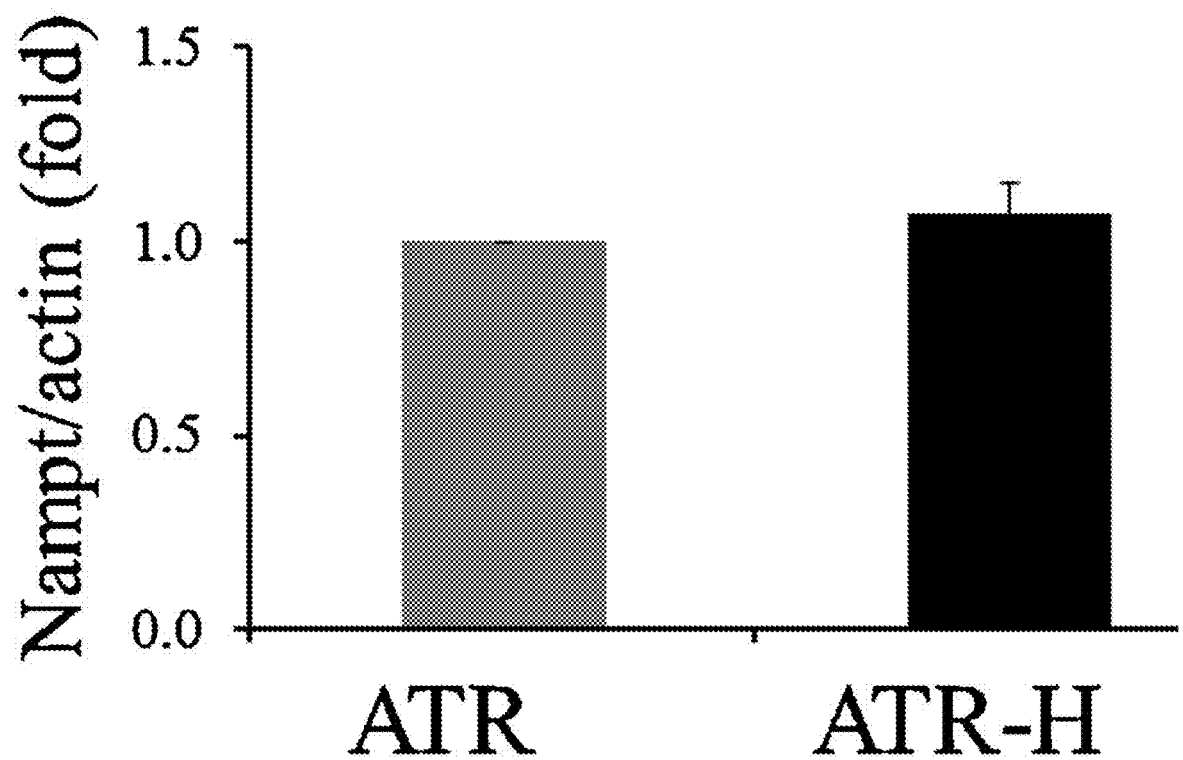

CBS, CSE, and 3-MST protein expression is lower in the hypomorphic ATR-H mutants compared to wild-type ATR cells. The lower $H_2S$ concentrations in the ATR-H cells raised the possibility that CBS, CSE, and 3-MST proteins levels might be altered in these cells compared to the wild-type ATR cells. The inventors employed western blotting to examine possible differences in protein expression of these enzymes in ATR and ATR-H cells. The inventors also examined the expression of nicotinamide phosphoribosyltransferase (Nampt), which may be co-regulated with CBS and CSE. As shown in FIG. 3A-3C, CBS, CSE, and 3-MST protein levels were all significantly lower in the ATR-H cells compared to the wild-type ATR cells. Importantly, Nampt levels were not significantly different between the two cell types, demonstrating that the hypomorphic ATR mutation does not affect Nampt protein expression (FIG. 3D). Based on this, the inventors conclude that wild-type ATR protein activity plays a role in the maintenance of the $H_2S$-synthesizng protein levels, but not that of Nampt.

Figure 4A:
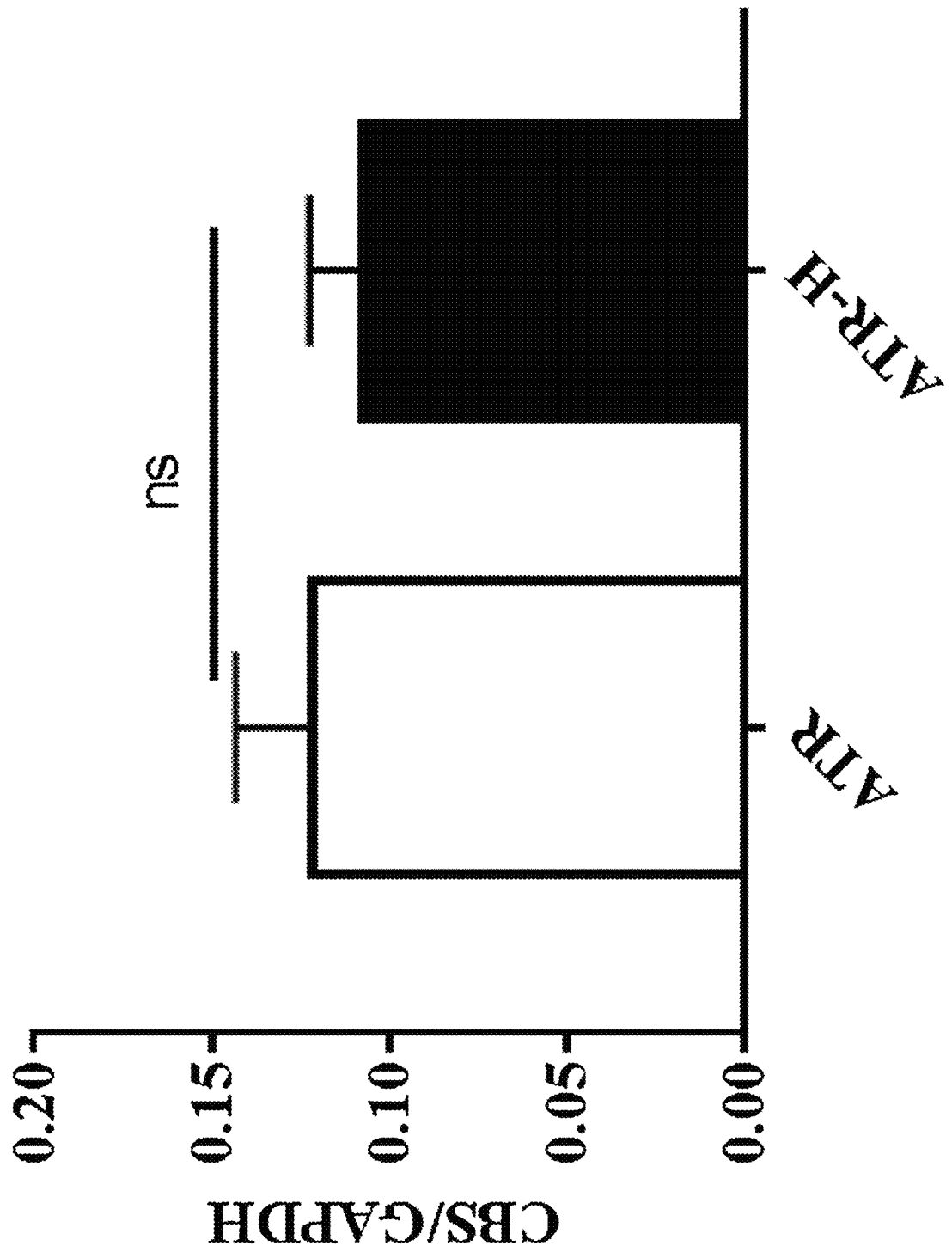
FIGS. 4A-4C show FIG. 4. Quantitative real-time polymerase chain reaction analyses of CBS (FIG. 4A), CSE (FIG. 4B), and 3-MST (FIG. 4C) mRNA levels in the ATR and ATR-H cell lines. Statistical analyses revealed no significant differences between CBS, CSE, and 3-MST mRNA levels between the two cell lines.
Figure 4B:
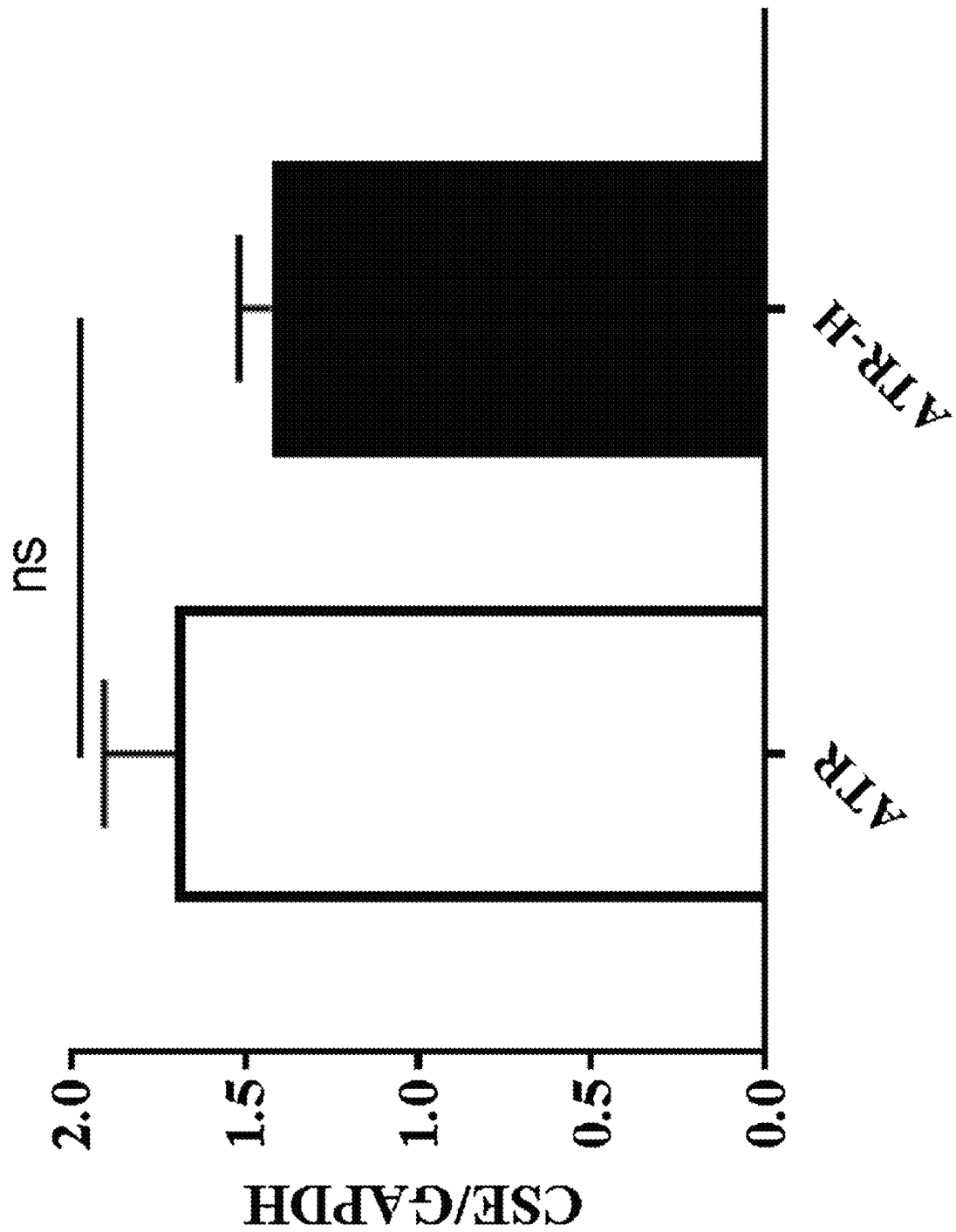
Figure 4C:
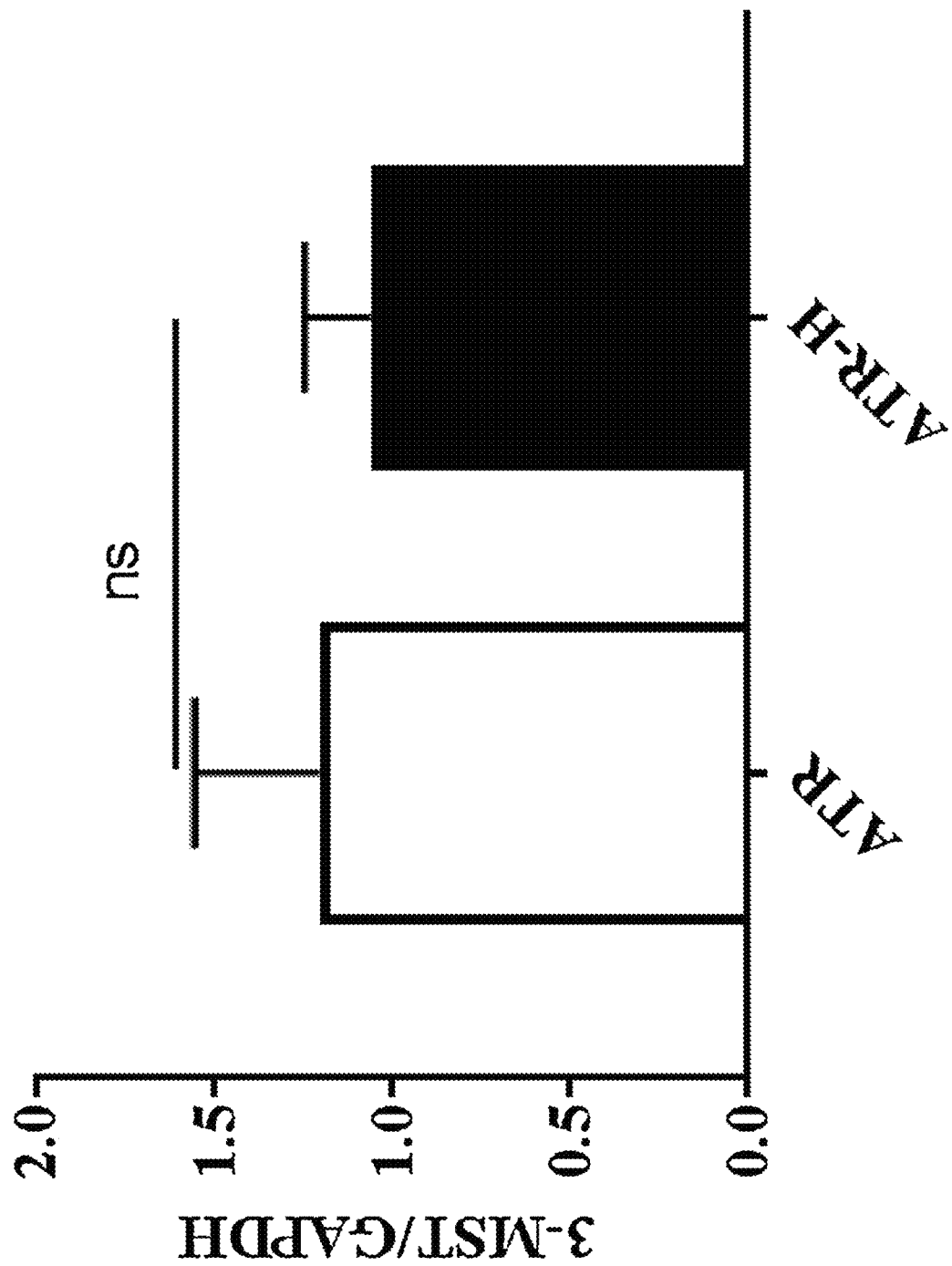

CBS, CSE, and 3-MST mRNA are not significantly different in the ATR-H cells compared to ATR cells. Since CBS, CSE, and 3-MST protein levels were lower in the ATR-H cells compared to the ATR cells, the inventors examined mRNA levels of each of these genes in the two cell types using GADPH mRNA as a control. As shown in FIGS. 4A-4C, the levels of each mRNA where reduced in the ATR-H cells compared to the ATR cells, but not significantly lower. Based on these data we conclude that the CBS, CSE, and 3-MST protein levels are lower in the ATR-H cell line due to either a lower rate of protein translation or decreased protein stabilities in the ATR-H cell line.

Figure 5A:
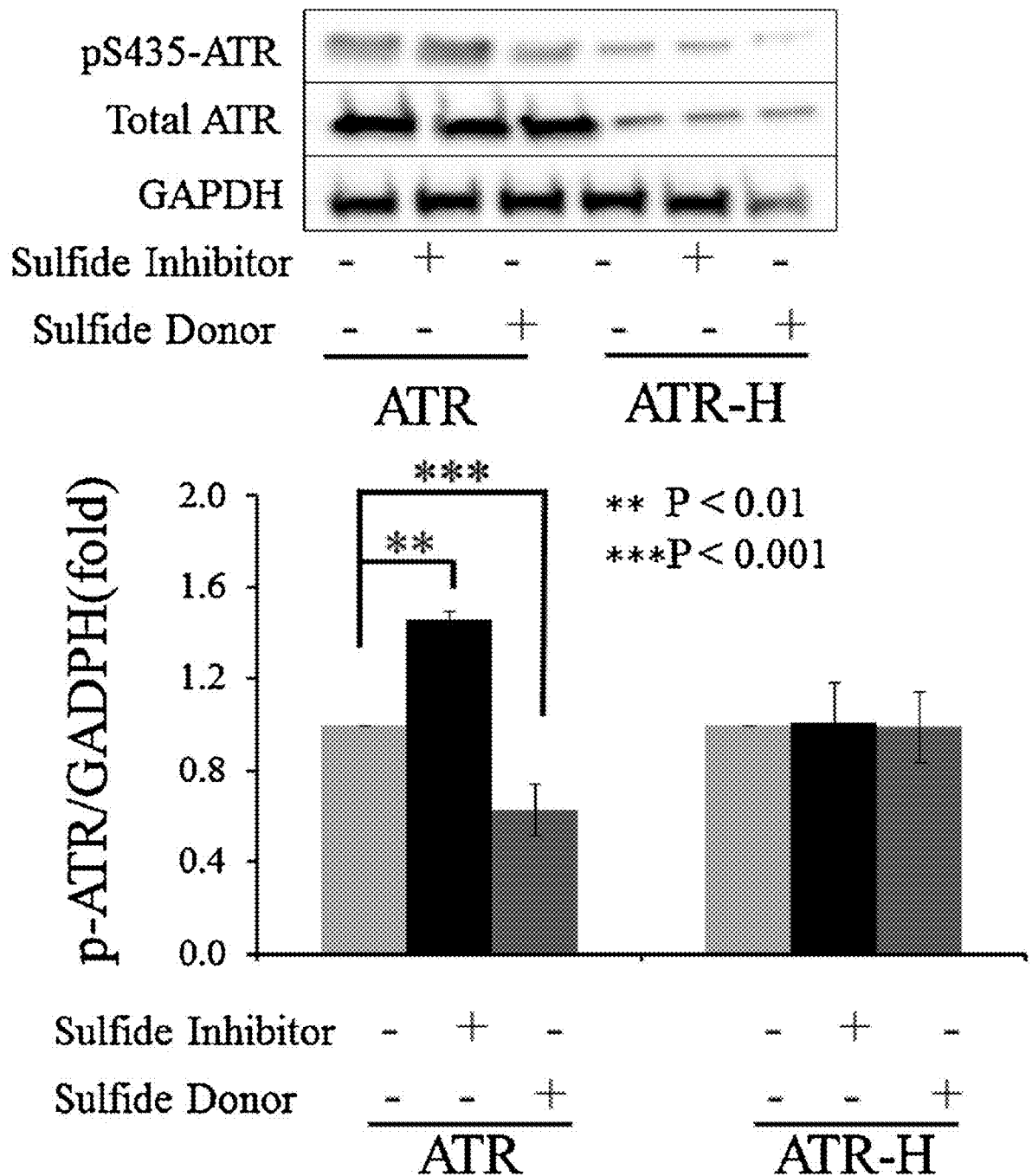
FIGS. 5A-5C show ATR protein phosphorylation on serine-435 with an $H_2S$ donor and inhibitor, or t-BOOH treatments. ATR and ATR-H cells were treated with 1 mM β-cyano)-l-alanine or 20 μM diallyl trisulfide for two hours and harvested (5 A).
Figure 5B:
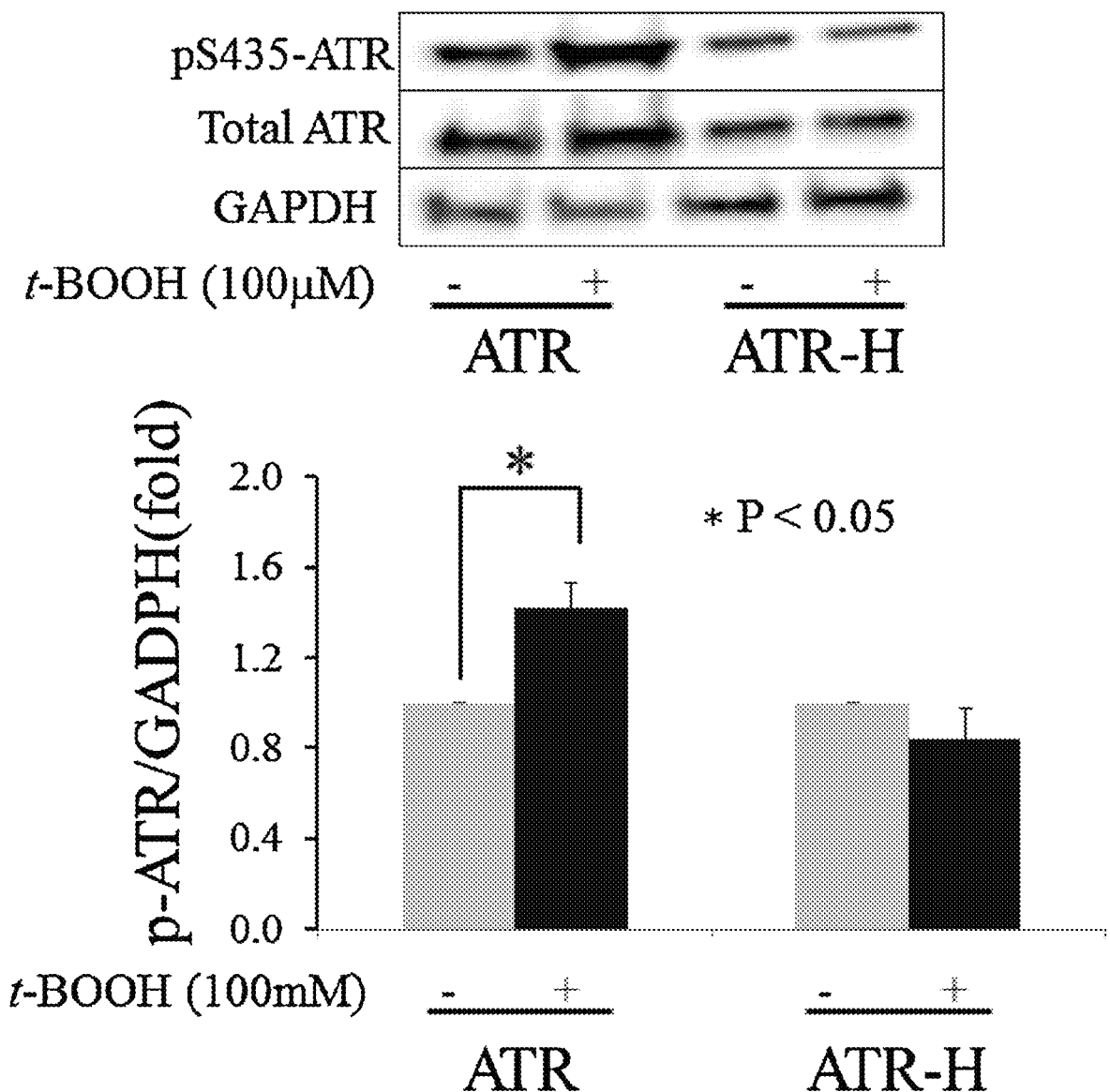
Figure 5C:
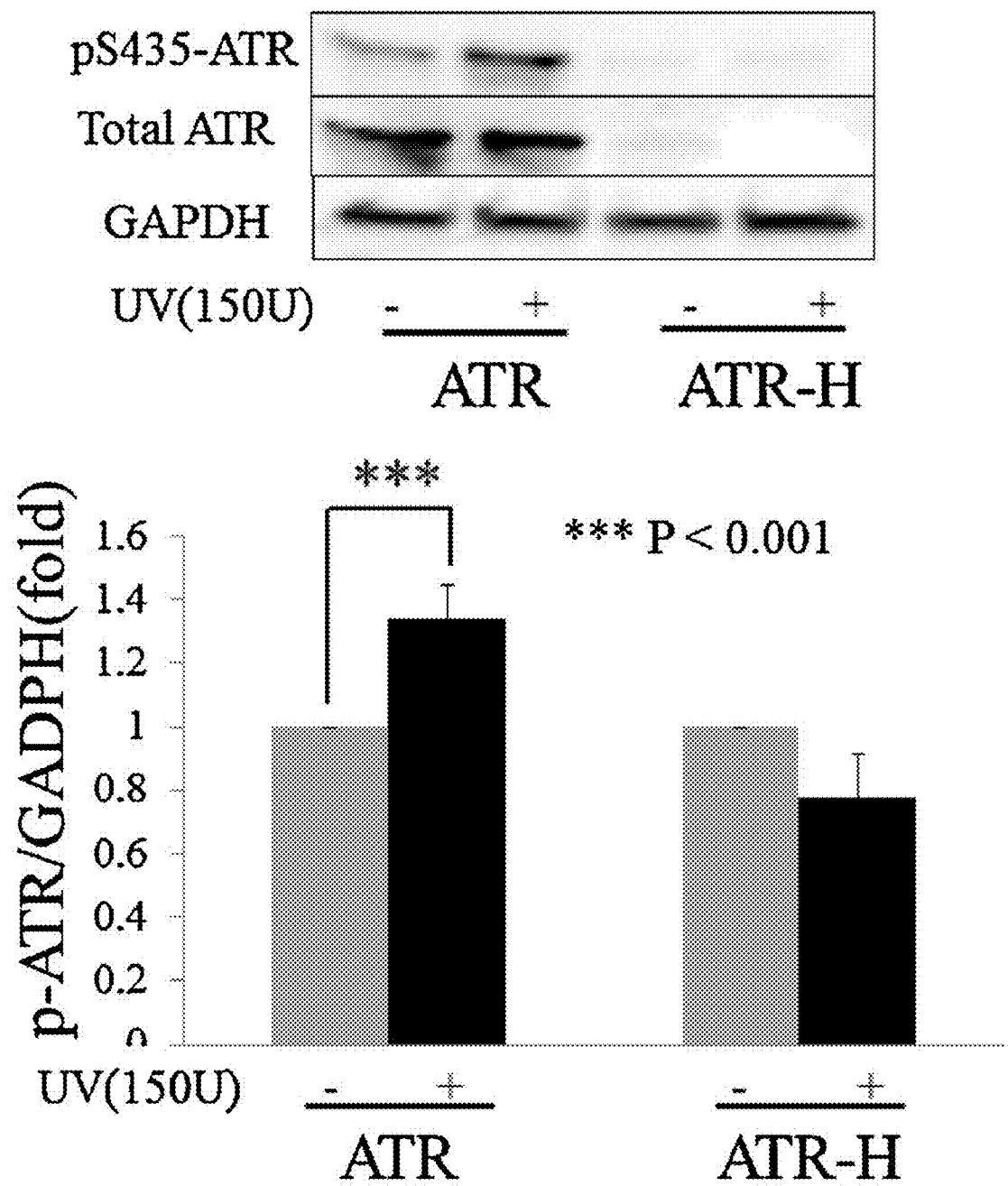

$H_2S$ inhibitor or donor exposures modulate ATR protein serine 435 phosphorylation in the ATR wild-type cells. The ATR kinase is partially regulated by phosphorylations on serine 435 and threonine 1989, with these phosphorylations correlating with kinase activation and with ATR-pS435 also promoting nucleotide excision repair at sites of photodamaged DNA. Since the above data supports a role for the ATR kinase regulating $H_2S$, the inventors hypothesized that $H_2S$ may in turn regulate ATR activity. To test this, the inventors employed an anti-ATR-p5435 antibody and performed western blots on ATR and ATR-H cells following a 2 h treatment with either 1 mM β-cyano-l-alanine (an $H_2S$ inhibitor), or 20 µM diallyl trisulfide (an $H_2S$ donor). As shown in FIG. 5A, β-cyano-l-alanine increased ATR-pS435 in the wild-type cells, while diallyl trisulfide inhibited this phosphorylation. In the ATR-H cells, ATR-pS435 levels were low and not affected by any treatment, indicating that the hypomorphic ATR mutation lacks a normal phosphorylation pattern on this amino acid moiety. To examine the possibility that ATR-pS435 was modulated by the $H_2S$ inhibitor and donor at a low level, in FIG. 5A the ratio of ATR-H-pS435/GAPDH protein levels was designated as one unit in the western blot graph and this measurement was compared to the ATR-H-pS435/GAPDH levels in the ATR-H cells treated with the $H_2S$ inhibitor or donor. No changes in ATR-H-pS435 were detected in the ATR-H cells (FIG. 5A). The ATR-pS435/GAPDH ratio was also used to analyze the ATR cells treated with the $H_2S$ inhibitor and donor, t-BOOH, and UV (FIGS. 5A-5C).

Since the $H_2S$ inhibitor β-cyano-l-alanine increased ATR-pS435 by ~50% compared to untreated cell phosphorylation levels, we treated ATR and ATR-H cells with 100 µM t-BOOH for 15 min, incubated the cells in media for 45 more minutes, and examined ATR-pS435 levels. As shown in FIG. 5B, this treatment induced ATR-pS435 levels ~50% in ATR wild type cells, indicating that with moderate oxidative stress, ATR-pS435 levels change roughly as much as does $H_2S$ synthesis inhibition. The ATR-H cells again showed minimal ATR-pS435 that was not increased by t-BOOH exposure (FIG. 5B). As in FIG. 4A, an untreated ATR-H-pS435/GAPDH ratio designated as one unit in the western blot graph was compared to the other ATR-H cell treatments (FIG. 5B).

ATR-pS435 regulates nucleotide excision repair at sites of DNA photodamage and is increased following UV exposure. We next treated ATR and ATR-H cells with 15,000 pJ/cm² UV light. As shown in FIG. 5C, ATR cell UV treatment resulted in increased ATR-pS435 levels. No serine 435 phosphorylation increase was seen in the UV treated ATR-H cells (FIG. 5C). As in FIGS. 5A and 5B, the untreated ATR-H-pS435/GAPDH ratio was designated as one unit in the western blot graph and compared to the UV treated ATR-H cells. In FIG. 5A-5C, whole ATR protein levels were also examined. When the ATR-pS435/whole ATR and ATR-H-pS435/whole ATR protein ratios were examined and analyzed in the same manner as the ATR-pS435/actin and ATR-H-pS435/actin ratios, the changes in ATR serine 435 phosphorylation levels were the same following $H_2S$ donor and inhibitor, t-BOOH, and UV treatments, while those in the ATR-H cells did not change.

Based on the above data, the inventors concluded that both $H_2S$ inhibitor or $H_2S$ donor modulate ATR serine 435 phosphorylation in the wild type, but not the ATR-H Seckel hypomorphic mutant cells. Additionally, since UV light also induces this phosphorylation, $H_2S$ appears to play an important role in regulating nucleotide excision repair by the ATR protein.

Figure 6:
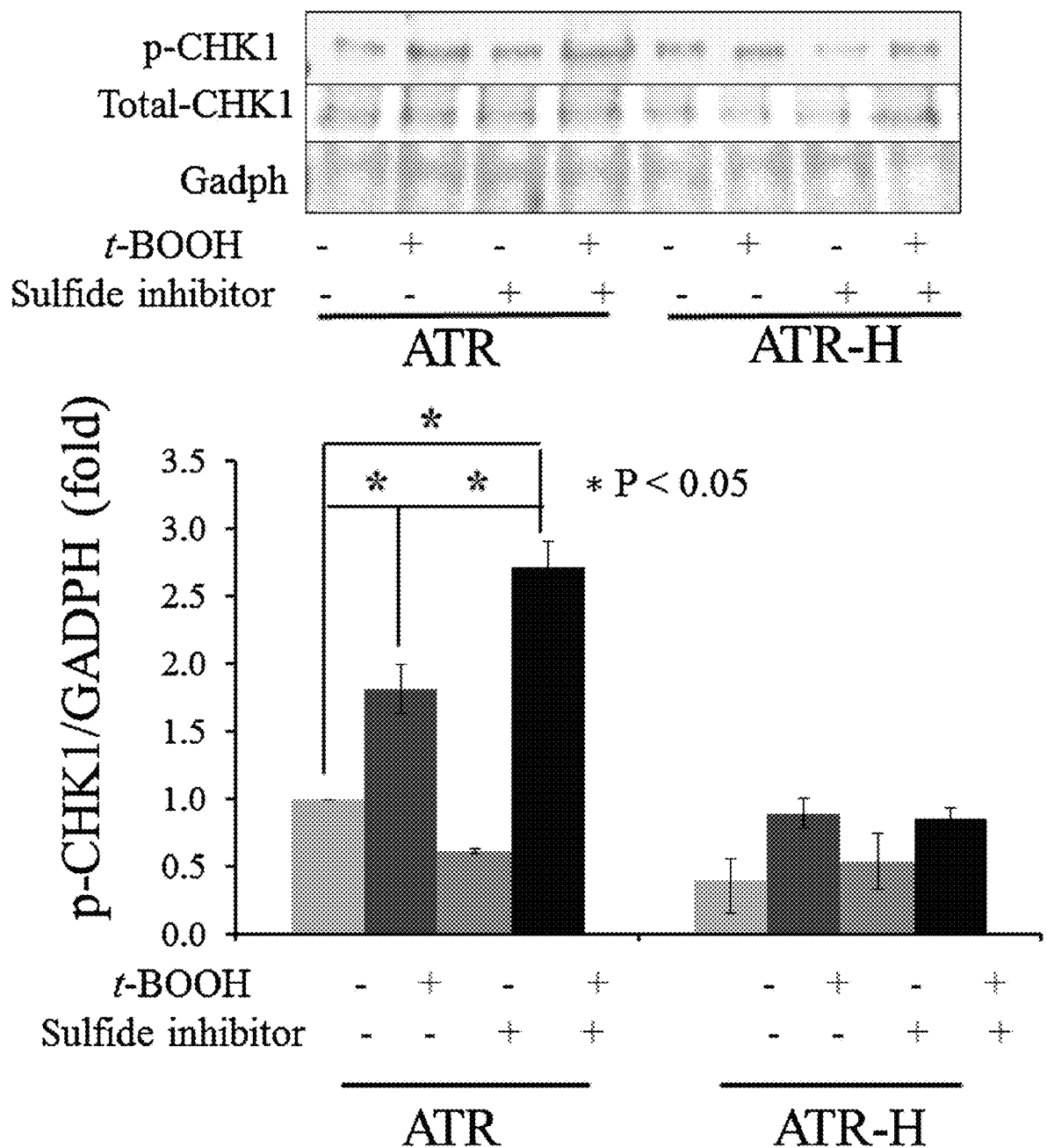
FIG. 6 shows CHK1 serine 345 phosphorylation in ATR and ATR-H cells with $H_2S$ synthesis inhibition followed by t-BOOH treatment was examined. ATR and ATR-H cells were pretreated with 1 mM β-cyanol-l-alanine for two hours, then 15 min with 10 μM t-BOOH, and harvested following a 45-minute incubation in standard media.

Induction of CHK1 serine 345 phosphorylation by t-BOOH exposure is modulated by H2S inhibitor pretreatment. The ATR kinase specifically phosphorylates CHK1 on serine 345, an event required for checkpoint-mediated cell cycle arrest and for faithful chromosomal segregation during mitosis. Based on the data presented above, the invnetors hypothesized that $H_2S$ synthesis inhibition by β-cyano-l-alanine would augment CHK1 serine-345 phosphorylation. The inventors examined CHK1 serine-345 phosphorylation in ATR and ATR-H cells, with and without a 2 h pretreatment with 1 mM β-cyano-l-alanine followed by a low 10 µM t-BOOH exposure for 15 min, followed by cell harvest at 45 min. As shown in FIG. 6, pretreatment of ATR cells with 1 mM β-cyano-l-alanine significantly increased CHK1 serine-345 phosphorylation following a 15-minute 10 µM t-BOOH exposure, compared to the same t-BOOH treatment without the β-cyano-l-alanine pretreatment. Thus, modulation of intracellular $H_2S$ can also alter oxidative stress-induced ATR kinase activity. The hypomorphic ATR-H mutants failed to show significant CHK1 serine-345 phosphorylation level changes with any treatment (FIG. 6). $H_2S$ donor pretreatment did not significantly alter CHK1 serine-345 phosphorylation levels in the ATR wild-type cells following t-BOOH treatment. Since $H_2S$ is rapidly converted into other portions of the cellular sulfur pool, which can exert both pro-oxidant and anti-oxidant effects, these results are being further analyzed in the inventors' lab. In this experiment, the inventors also included a whole CHK1 protein control. CHK1 protein levels did not show significant variation between the ATR and ATR-H cells. For this reason, the inventors designated the untreated ATR cell CHK1 phospho-serine-345/GADPH ratio as one unit on the western blot and compared this ratio to all other treatments of the ATR and ATR-H cells. When the untreated ATR cell CHK1 phospho-serine-345/whole CHK1 protein ratio was used, the changes in the CHK1 phosphorylation were the same as with the GAPDH control. Thus, whole CHK1 or GAPDH proteins were thus equally useful as western blot loading controls. Based on these observations, pharmacologic suppression of cellular $H_2S$ potentiates ATR kinase activity following oxidant exposure. This potentiation is not seen in the ATR-H hypomorphic mutant cells.

$H_2S$ Synthesis Inhibition Preferentially Increases dsDNA Breaks in ATR-H Cells by Itself and when Combined with t-BOOH Treatment.

Figure 7:
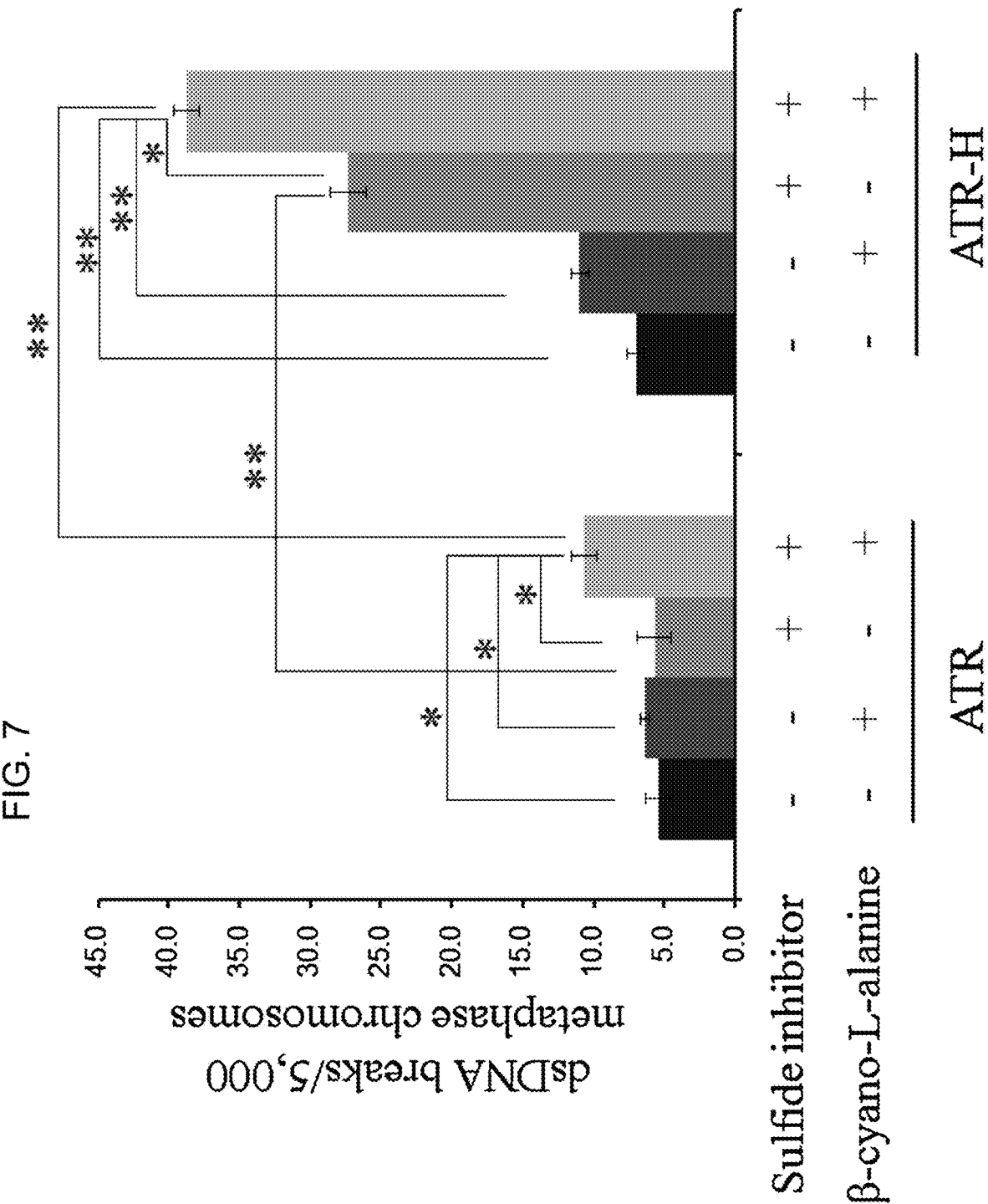
FIG. 7. shows dsDNA break formation in ATR and ATR-H cells following $H_2S$ synthesis inhibition. ATR and ATR-H cells were pretreated with 1 mM cyanol-l-alanine for two hours, then 15 min with t-BOOH, cultured one hour in standard media, treated with colcemid for four hours, and harvested. dsDNA breaks in Giemsa stained, Colcemid-treated cells, were counted under oil immersion microscopy. The t-BOOH concentration was 10 μM.

During S-phase ATR prevents stalled replication forks from degenerating in dsDNA breaks. Since $H_2S$ regulates several ATR functions and the ATR-H cells show reduced $H_2S$ metabolism and increased oxidant sensitivity (see above), the inventors hypothesized that $H_2S$ inhibition would preferentially effect genomic stability in ATR-H cells following oxidative stress. To do this the inentors examined dsDNA breaks by oil immersion microscopy in metaphase colcem id-blocked, Giemsa stained, metaphase chromosomal preparations pretreated with or without an $H_2S$ inhibitor (1 mM β-cyano-l-alanine), t-BOOH, or both combined. The inventors chose this method of dsDNA quantification, as enzymatic methods to measure DNA damage often depend on correctly functioning DNA repair enzymes, which are at least partially dysregulated in the ATR-H cells, making the assay results meaningless. As shown in FIG. 7, 10 μM t-BOOH treatment alone significantly increased dsDNA break formation in ATR-H cells, but not the ATR cells. However, a two-hour pretreatment with the $H_2S$ inhibitor followed by t-BOOH treatment significantly increased dsDNA breaks in both cells types. Interestingly, $H_2S$ inhibition alone significantly increased dsDNA breaks in ATR-H cells, but not in the ATR wild type cells (FIG. 7). Additionally the number of breaks was much higher in the ATR-H cells compared to the ATR cells. Since an $H_2S$ donor did not alter CHK1 serine-345 phosphorylation, it was not analyzed by dsDNA break studies. These findings indicate that upon being stressed by pharmacologic $H_2S$ inhibition alone or pharmacologic $H_2S$ inhibition combined with oxidative stress, the ATR-H cells show increased genomic instability. These data suggest that $H_2S$ likely plays a role in the maintenance of genomic stability by the ATR protein kinase.

Discussion

The inventors show for the first time that the hypomorphic Seckel syndrome type 1 ATR mutation causes lower cellular $H_2S$ concentrations compared to syngeneic ATR kinase wild type cells. ATR cell treatment with the pharmacologic ATR inhibitor NU6027 also lowered cellular $H_2S$ concentrations in the ATR, but not ATR-H cells. Additionally, treating ATR cells with the $H_2S$ donor diallyl trisulfide suppressed ATR cell $H_2S$ levels, but not in the ATR-H cells. Last, the CBS and CSE inhibitor β-cyano-1-alanine lowered $H_2S$ levels in both cell types. Taken together, this data indicates that the ATR kinase regulates cellular $H_2S$ concentrations. It also demonstrates that there are two loci of $H_2S$ concentration control: 1) the activities of the CBS and CSE enzymes and 2) the functioning of the ATR kinase. The observation that diallyl trisulfide suppressed $H_2S$ concentrations in the ATR, but not ATR-H cells, suggests that ATR may have a role in responding to excess $H_2S$ levels. However, as the $H_2S$ levels are already low in the ATR-H cells, the lack of suppression may be due to the ATR-H cells not biochemically requiring further $H_2S$ level suppression.

The ATR-H cells were more sensitive to the toxic effects of t-BOOH in the CEFA compared to wild-type cells, demonstrating that the hypomorphic ATR mutation causes deficits in cellular anti-oxidant responses. Additionally, $H_2S$ inhibitor treatment combined with t-BOOH preferentially lowered ATR-H cell colony formation and interestingly, the $H_2S$ inhibitor by itself, suppressed colony formation in the ATR-H, but not the ATR cells. The $H_2S$ donor exerted toxic effects on both cell types, with preferential toxicity observed in the ATR-H cells. Thus, different patterns between the two cells lines were seen. In the ATR cells, the $H_2S$ inhibitor only significantly potentiated t-BOOH toxicity at the two higher doses, while in the ATR-H cells 200 μM t-BOOH and $H_2S$ inhibitor pretreatment with 200 μM t-BOOH were also not significantly different. These findings are likely due to 50 μM t-BOOH being too small a dose to significantly affect the ATR cells, even with the inhibitor pretreatment. The lack of a significant difference the ATR-H cells treated with 200 μM t-BOOH, with and without the $H_2S$ inhibitor, may be due to this higher t-BOOH dose being highly toxic to the hypomorphic mutant cells, making the biochemical contribution of the $H_2S$ inhibitor insignificant. However, taken together these results indicate that the perturbations in $H_2S$ metabolism seen in the ATR-H cells makes them more vulnerable to the toxic effects of t-BOOH when combined with pharmacologic alterations in cellular $H_2S$ metabolism.

These data implied that the function of ATR in the maintenance of genomic stability might be compromised in the ATR-H mutant cells. Direct measurements of dsDNA breaks by oil immersion microscopy revealed that the hypomorphic ATR-H mutant cells where significantly more vulnerable to dsDNA break formation than wild type cells following $H_2S$ inhibitor pretreatment, followed both with and without subsequent 10 μM t-BOOH treatment. Interestingly, $H_2S$ inhibitor treatment alone significantly induced dsDNA breaks in the ATR-H cells, but not the wild-type cells. As expected, there was a positive correlation between dsDNA breaks in the ATR-H cells with $H_2S$ synthesis inhibition, both with and without t-BOOH treatment. Lower dsDNA breaks were seen in the ATR cells, likely due to the very low 10 μM t-BOOH dose employed. This data suggests that when cellular $H_2S$ levels fall to very low levels, the ability to maintain genomic integrity is compromised, and even exacerbated in the ATR-H cell line. Our data also implies that exogenous $H_2S$ may induce DNA damage.

The ATR-H cells also had statistically significant lower CBS, CSE, and 3-MST protein expression levels compared to wild type cells, while Nampt levels were the same. Although here we did not examine the enzymatic activities of these proteins, possibly the lower ATR-H $H_2S$ levels are due to less protein present to synthesize $H_2S$.1 Examination of CBS, CSE, and 3-MST mRNA levels between the two cell lines did not show significant differences in mRNA expression levels for these gene products. Based on this it is likely that the levels of the $H_2S$-synthesizing protein are lower in the ATR-H cells due to lower protein stabilities or decreased mRNA translation.

We next examined the effects of $H_2S$ donors and synthesis inhibitors on ATR phosphorylation. The $H_2S$ donor suppressed ATR-pS435 in the ATR cells, while the $H_2S$ synthesis inhibitor increased it, demonstrating that cellular $H_2S$ concentrations modulate this phosphorylation. These changes were not seen in the ATR-H cells. Control experiments demonstrated that t-BOOH and UV exposure also induced this phosphorylation in ATR, but not ATR-H cells. Based on these observations $H_2S$ bioavailability plays a role in regulating ATR kinase activation and may modulate its role in nucleotide excision repair. Additionally, since this phosphorylation correlates with ATR kinase activation and is suppressed by increased $H_2S$ levels and increased by low $H_2S$ levels, our results suggest that increased ATR-pS435 may function sensing and responding to changes in cellular $H_2S$ concentrations. Last, the ATR-mediated serine 345 CHK1 phosphorylation induced by a low concentration of t-BOOH treatment was potentiated by pretreatment with an $H_2S$ inhibitor, further confirming ATR kinase activity itself, is modulated by cellular $H_2S$ concentrations. Thus, ATR-initiated signal transduction is linked to cellular $H_2S$ bioavailability and metabolism.

ATR regulates intra-S-phase and G2/M-phase checkpoints via CHK1 phosphorylation, stabilizes stalled replication forks, preventing dsDNA break formation, promotes homologous recombination, regulates replication origin firing at specialized start sites, and promotes faithful chromosomal segregation during mitosis. The later function likely depends on the CHK1 serine 345 phosphorylation. The data presented here implies that $H_2S$ plays a role in regulating these ATR kinase-dependent functions via regulating this phosphorylation. Additionally, ATR inhibitors are being examined in preclinical and clinical studies as single agents, or paired with radiotherapy, as novel cancer therapies. Increased $H_2S$ cellular concentrations promote cancer cell growth in several different cancer types, although very high concentrations of $H_2S$ exert cytotoxic effects. Our data suggests that ATR inhibitors could exert anti-cancer effects, in part, as $H_2S$ synthesis inhibitors. Additionally, since an $H_2S$ donor attenuated the ATR serine 435 phosphorylation and this phosphorylation is necessary for ATR activation, and ATR activity is necessary for cell survival, high $H_2S$ levels may contribute to cell death via inhibition of ATR kinase function and activation.

Figure 8:
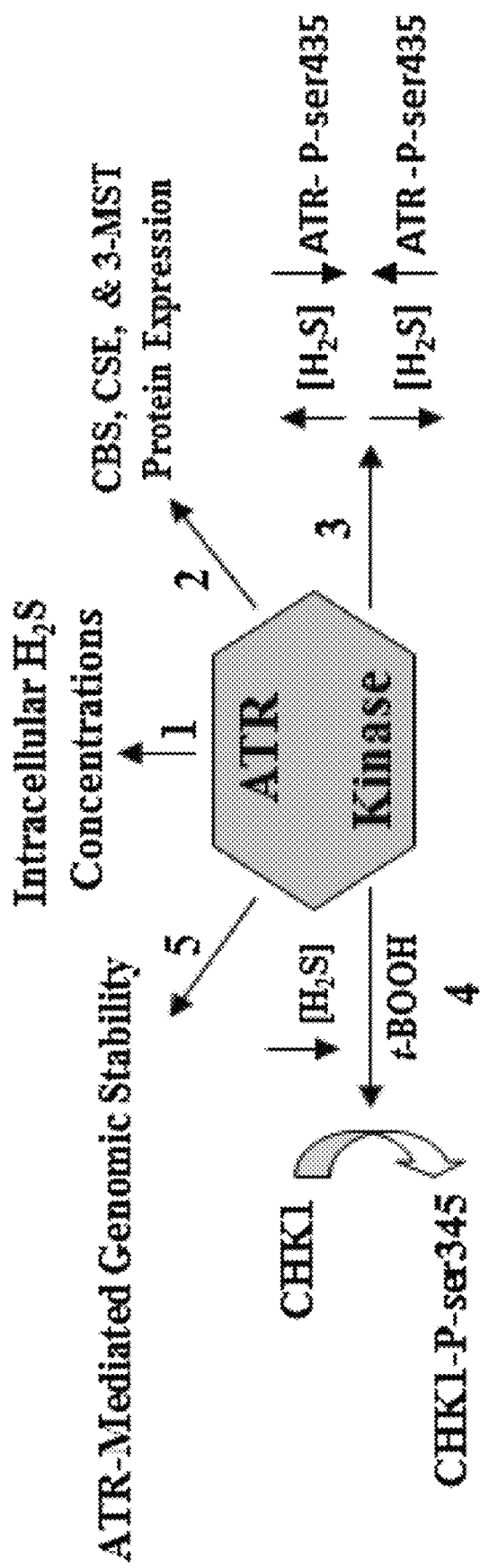
FIG. 8 shows a summary of the findings disclosed herein. The ATR kinase regulates intracellular $H_2S$ concentrations (arrow 1) and the levels of the three $H_2S$-synthesizing enzymes (arrow 2). Increased in intracellular $H_2S$ concentrations decreased ATR serine 435 phosphorylation, while decreased in intracellular $H_2S$ concentrations increased this phosphorylation (arrow 3). Attenuation of intracellular $H_2S$ synthesis also potentiates CHK1 serine 345 phosphorylation following ATR cell exposure to low t-BOOH concentration, an event not seen in ATR-H cells (arrow 4). Lastly, low cellular $H_2S$ concentrations in the hypomorphic ATR-H cells increase genomic instability by itself, and when combined with a low dose of t-BOOH. Taken together, our data suggests that the ATR kinase regulates and is in turn regulated by $H_2S$.

Disclosed herein, the inventors present for the first time that a major constituent of the DDR, the ATR kinase, regulates and is regulated by intracellular $H_2S$ concentrations. These findings represent a deeper understanding of $H_2S$ regulation of cell survival and are summarized in FIG. 8. Additionally, many ATR and CHK1-dependent cellular functions, such as nucleotide excision repair, cellular checkpoint initiation, and chromosomal segregation during mitosis, may also be regulated by intracellular $H_2S$ concentrations.

The evidence indicates that specific diseases will be treated by ATR kinase promotors, including Neurodegenerative disease, type II diabetes, coronary vascular disease, and aging. The dosage for these treatments is expected to be around 1-10 microM ATR kinase promotors.

Based on the biochemistry, ATR kinase inhibitors are evidenced to be a general cancer therapeutic. The more aggressive/high-grade tumors would be ideal for this treatment, as highly aggressive/widely metastatic tumors will be more vulnerable to this treatment. The dosage for these treatments would preferably be between 1-500 microM, more preferably between 1-10 microM of ATR kinase inhibitors.

Based on the evidence, it is expected that a combination of an ATR inhibitor giver with a cystathionine beta-synthase (CBS) and/or a cystathionine gamma-lyase (CSE) inhibitor, would be even more effective to treat cancer, especially very aggressive cancers. The dosage for these treatments would treatments would preferably be between 100 nanoM-500 microM, more preferably between 1-10 microM of ATR kinase inhibitors, and 10-500 microM CBS and CSE inhibitors.

Further, the evidence indicates there independent value in moderating the H2S bioavailability level with ATR kinase promotor/inhibitor administration in slowing down the detrimental effects of aging.

Pharmaceutical Compositions

The methods described herein can also include the administrations of pharmaceutically acceptable compositions that include the therapeutic, or a pharmaceutically acceptable salt, solvate, or prodrug thereof. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention can be administered alone, or in a mixture, in the presence of a pharmaceutically acceptable excipient or carrier. The excipient or carrier is selected on the basis of the mode and route of administration. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The methods described herein can include the administration of a therapeutic, or prodrugs or pharmaceutical compositions thereof, or other therapeutic agents. Exemplary therapeutics include those that promote ATR kinase action (including TopBP1) and those that decrease ATF kinase action (including NU6027).

The pharmaceutical compositions can be formulated so as to provide immediate, extended, or delayed release of the active ingredient after administration to the patient by employing procedures known in the art.

The compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or, from about 100 mg to about 250 mg of the active ingredient. For preparing solid compositions such as tablets, the principal active ingredient is mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palm itostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions suitable for oral mucosal administration (e.g., buccal or sublingual administration) include tablets, lozenges, and pastilles, where the active ingredient is formulated with a carrier, such as sugar, acacia, tragacanth, or gelatin and glycerine.

Coatings

The pharmaceutical compositions formulated for oral delivery, such as tablets or capsules of the present invention can be coated or otherwise compounded to provide a dosage form affording the advantage of delayed or extended release. The coating may be adapted to release the active drug substance in a predetermined pattern (e.g., in order to achieve a controlled release formulation) or it may be adapted not to release the active drug substance until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the drug is released in the lower gastrointestinal tract.

In addition to coatings that effect delayed or extended release, the solid tablet compositions may include a coating adapted to protect the composition from unwanted chemical changes (e.g., chemical degradation prior to the release of the active drug substance). The coating may be applied on the solid dosage form.

Parenteral Administration

Within the scope of the present invention are also parenteral depot systems from biodegradable polymers. These systems are injected or implanted into the muscle or subcutaneous tissue and release the incorporated drug over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 µm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Mucosal Drug Delivery

Mucosal drug delivery (e.g., drug delivery via the mucosal linings of the nasal, rectal, vaginal, ocular, or oral cavities) can also be used in the methods described herein. Methods for oral mucosal drug delivery include sublingual administration (via mucosal membranes lining the floor of the mouth), buccal administration (via mucosal membranes lining the cheeks), and local delivery.

Oral transmucosal absorption is generally rapid because of the rich vascular supply to the mucosa and allows for a rapid rise in blood concentrations of the therapeutic.

For buccal administration, the compositions may take the form of, e.g., tablets, lozenges, etc. formulated in a conventional manner. Permeation enhancers can also be used in buccal drug delivery. Exemplary enhancers include 23-lauryl ether, aprotinin, azone, benzalkonium chloride, cetylpyridinium chloride, cetyltrimethylammonium bromide, cyclodextrin, dextran sulfate, lauric acid, lysophosphatidylcholine, methol, methoxysalicylate, methyloleate, oleic acid, phosphatidylcholine, polyoxyethylene, polysorbate 80, sodium EDTA, sodium glycholate, sodium glycodeoxycholate, sodium lauryl sulfate, sodium salicylate, sodium taurocholate, sodium taurodeoxycholate, sulfoxides, and alkyl glycosides. Bioadhesive polymers have extensively been employed in buccal drug delivery systems and include cyanoacrylate, polyacrylic acid, hydroxypropyl methylcellulose, and poly methacrylate polymers, as well as hyaluronic acid and chitosan.

Liquid drug formulations (e.g., suitable for use with nebulizers and liquid spray devices and electrohydrodynamic (EHD) aerosol devices) can also be used. Other methods of formulating liquid drug solutions or suspension suitable for use in aerosol devices are known to those of skill in the.

Formulations for sublingual administration can also be used, including powders and aerosol formulations. Exemplary formulations include rapidly disintegrating tablets and liquid-filled soft gelatin capsules.

Dosing Regimes

The present methods for treating $H_2S$ related diseases are carried out by administering a therapeutic for a time and in an amount sufficient to result in decreased H2S bioavailability or increased H2S bioavailability depending on the disease and/or decrease in one or more symptoms of the $H_2S$ related disease.

The amount and frequency of administration of the compositions can vary depending on, for example, what is being administered, the state of the patient, and the manner of administration. In therapeutic applications, compositions can be administered to a patient suffering from $H_2S$ related diseases in an amount sufficient to relieve or least partially relieve the symptoms of the $H_2S$ related diseases and its complications. The dosage is likely to depend on such variables as the type and extent of progression of the $H_2S$ related diseases, the severity of the $H_2S$ related diseases, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of the $H_2S$ related diseases or slowing its progression.

The amount of therapeutic per dose can vary. For example, a subject can receive from about 0.1 µg/kg to about 10,000 µg/kg. Generally, the therapeutic is administered in an amount such that the peak plasma concentration ranges from 150 nM-250 µM.

Exemplary dosage amounts can fall between 0.1-5000 µg/kg, 100-1500 µg/kg, 100-350 µg/kg, 340-750 µg/kg, or 750-1000 µg/kg. Exemplary dosages can 0.25, 0.5, 0.75, 1°, or 2 mg/kg. In another embodiment, the administered dosage can range from 0.05-5 mmol of therapeutic (e.g., 0.089-3.9 mmol) or 0.1-50 µmol of therapeutic (e.g., 0.1-25 µmol or 0.4-20 µmol).

The plasma concentration of therapeutic can also be measured according to methods known in the art. Exemplary peak plasma concentrations of therapeutic can range from 0.05-10 µM, 0.1-10 µM, 0.1-5.0 µM, or 0.1-1 µM. Alternatively, the average plasma levels of therapeutic can range from 400-1200 µM (e.g., between 500-1000 µM) or between 50-250 µM (e.g., between 40-200 µM). In some embodiments where sustained release of the drug is desirable, the peak plasma concentrations (e.g., of therapeutic) may be maintained for 6-14 hours, e.g., for 6-12 or 6-10 hours. In other embodiments where immediate release of the drug is desirable, the peak plasma concentration (e.g., of therapeutic) may be maintained for, e.g., 30 minutes.

The frequency of treatment may also vary. The subject can be treated one or more times per day with therapeutic (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Kits

Any of the pharmaceutical compositions of the invention described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention to reduce symptoms and/or underlying cause of the $H_2S$ related diseases.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

We claim:

1. A pharmaceutical composition comprising:
   a first therapeutic; and
   a second therapeutic;
   wherein the first therapeutic is one of an ATR kinase promotor and an ATR kinase inhibitor; and
   the first therapeutic is chemically distinct from the second therapeutic.

2. The pharmaceutical composition of claim 1 wherein the first therapeutic is the ATR kinase promotor.

3. The pharmaceutical composition of claim 1 wherein the first therapeutic is the ATR inhibitor.

4. The pharmaceutical composition of claim 1 wherein the second therapeutic is a H2S promotor.

5. The pharmaceutical composition of claim 1 wherein the second therapeutic is a H2S inhibitor.

6. The pharmaceutical composition of claim 1 wherein, the second therapeutic is a cystathionine beta-synthase (CBS) inhibitor.

7. The pharmaceutical composition of claim 1 wherein, the second therapeutic is a cystathionine gamma-lyase (CSE) inhibitor.

8. The pharmaceutical composition of claim 2 wherein the ATR kinase promotor is one of ETAA1 (Ewing's tumor-associated antigen 1) and TopBP1.

9. The pharmaceutical composition of claim 3 wherein the ATR kinase inhibitor is one of NU6027, AZD6738, BAY1895344, VX-803, and VX-970.

10. The pharmaceutical composition of claim 1 wherein the first therapeutic is the ATR kinase promotor and the second therapeutic is a H2S promotor.

11. The pharmaceutical composition of claim 10 wherein the ATR kinase promotor is ETAA1 (Ewing's tumor-associated antigen 1).

12. The pharmaceutical composition of claim 10 wherein the ATR kinase promotor is TopBP1.

13. The pharmaceutical composition of claim 1 wherein the first therapeutic is the ATR inhibitor and the second therapeutic is a H2S inhibitor.

14. The pharmaceutical composition of claim 13 wherein the ATR kinase inhibitor is NU6027.

15. The pharmaceutical composition of claim 13 wherein the ATR kinase inhibitor is AZD6738.

16. The pharmaceutical composition of claim 13 wherein the ATR kinase inhibitor is BAY1895344.

17. The pharmaceutical composition of claim 13 wherein the ATR kinase inhibitor is VX-803.

18. The pharmaceutical composition of claim 13 wherein the ATR kinase inhibitor is VX-970.

19. The pharmaceutical composition of claim 3 wherein the second therapeutic is one of cystathionine beta-synthase (CBS) inhibitor, a cystathionine gamma-lyase (CSE) inhibitor, and a combination of a CBS inhibitor and a CSE inhibitor.

20. The pharmaceutical composition of claim 3 wherein the ATR kinase inhibitor is one of NU6027, AZD6738, BAY1895344, VX-803, and VX-970.

21. The pharmaceutical composition of claim 3 wherein the second therapeutic is a combination of a cystathionine beta-synthase (CBS) inhibitor and a cystathionine gamma-lyase (CSE) inhibitor.

\* \* \* \* \*

SEQUENCE LISTING

```
<160> NUMBER OF SEQ ID NOS: 8

<210> SEQ ID NO 1
<211> LENGTH: 18
<212> TYPE: DNA
<213> ORGANISM: Homo sapiens

<400> SEQUENCE: 1
acagtcagcc gcatcttc                                                    18

<210> SEQ ID NO 2
<211> LENGTH: 19
<212> TYPE: DNA
<213> ORGANISM: Homo sapiens

<400> SEQUENCE: 2
cgcccaatac gaccaaatc                                                   19

<210> SEQ ID NO 3
<211> LENGTH: 20
<212> TYPE: DNA
<213> ORGANISM: Homo sapiens

<400> SEQUENCE: 3
gcctttgctt caggtttagc                                                  20

<210> SEQ ID NO 4
<211> LENGTH: 19
<212> TYPE: DNA
<213> ORGANISM: Homo sapiens

<400> SEQUENCE: 4
ccttctgggt ggggtttgt                                                   19

<210> SEQ ID NO 5
<211> LENGTH: 18
<212> TYPE: DNA
```

```
<213> ORGANISM: Homo sapiens

<400> SEQUENCE: 5
aggatgaaca caggcaat                                                 18

<210> SEQ ID NO 6
<211> LENGTH: 20
<212> TYPE: DNA
<213> ORGANISM: Homo sapiens

<400> SEQUENCE: 6
aaaaacccaa acacgcaaac                                               20

<210> SEQ ID NO 7
<211> LENGTH: 18
<212> TYPE: DNA
<213> ORGANISM: Homo sapiens

<400> SEQUENCE: 7
accgtgaaca tcccctto                                                 18

<210> SEQ ID NO 8
<211> LENGTH: 20
<212> TYPE: DNA
<213> ORGANISM: Homo sapiens

<400> SEQUENCE: 8
ttcttctcct ggaacagatg                                               20
```